US010307723B2

(12) United States Patent
Burakowska-Meise et al.

(10) Patent No.: US 10,307,723 B2
(45) Date of Patent: Jun. 4, 2019

(54) PROCESS FOR PREPARING MICROCAPSULES HAVING A POLYUREA SHELL AND A LIPOPHILIC CORE MATERIAL

(71) Applicant: BASF SE, Ludwigshafen (DE)

(72) Inventors: Ewelina Burakowska-Meise, Reichenbach (DE); Wolfgang Denuell, Mannheim (DE); Thomas Soltys, Ludwigshafen (DE); Emmanuel Julien Leon Christian Aussant, Paris (FR); Addi Fadel, Paris (FR); Ian Harrison, Poissy (FR)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/524,642

(22) PCT Filed: Oct. 27, 2015

(86) PCT No.: PCT/EP2015/074825
§ 371 (c)(1),
(2) Date: May 5, 2017

(87) PCT Pub. No.: WO2016/071152
PCT Pub. Date: May 12, 2016

(65) Prior Publication Data
US 2017/0326522 A1    Nov. 16, 2017

(30) Foreign Application Priority Data

Nov. 7, 2014    (EP) ..................................... 14192185

(51) Int. Cl.
| | | |
|---|---|---|
| *B01J 13/18* | (2006.01) | |
| *B01J 13/20* | (2006.01) | |
| *A61K 8/11* | (2006.01) | |
| *A61K 8/84* | (2006.01) | |
| *A61K 9/50* | (2006.01) | |
| *C11D 3/37* | (2006.01) | |
| *D06M 15/564* | (2006.01) | |
| *D21H 21/06* | (2006.01) | |
| *C11D 17/00* | (2006.01) | |

(52) U.S. Cl.
CPC .............. *B01J 13/185* (2013.01); *A61K 8/11* (2013.01); *A61K 8/84* (2013.01); *A61K 9/5031* (2013.01); *B01J 13/20* (2013.01); *B01J 13/206* (2013.01); *C11D 3/3703* (2013.01); *C11D 17/0039* (2013.01); *D06M 15/564* (2013.01); *D21H 21/06* (2013.01)

(58) Field of Classification Search
CPC ........ B01J 13/185; B01J 13/20; B01J 13/206; A61K 8/11; A61K 8/84; A61K 9/5031; C11D 3/3703; C11D 17/0039; D06M 15/564; D21H 21/06
See application file for complete search history.

(56) References Cited

U.S. PATENT DOCUMENTS

| | | | |
|---|---|---|---|
| 4,193,889 A | 3/1980 | Baatz et al. | |
| 4,489,017 A | 12/1984 | Alberts et al. | |
| 5,225,118 A | 7/1993 | Juang et al. | |
| 5,342,556 A | 8/1994 | Traubel et al. | |
| 8,650,660 B2 | 2/2014 | Shi et al. | |
| 2003/0157170 A1 | 8/2003 | Liggins et al. | |
| 2004/0034162 A1 | 2/2004 | Laas et al. | |
| 2014/0331414 A1* | 11/2014 | Bone ........................ B01J 13/18 8/137 |

FOREIGN PATENT DOCUMENTS

| | | |
|---|---|---|
| EP | 0537467 A1 | 4/1993 |
| EP | 2 426 172 A1 | 3/2012 |
| EP | 2 648 211 A1 | 10/2013 |
| GB | 1371179 A | 10/1974 |
| WO | WO-01/94001 A2 | 12/2001 |
| WO | WO-03/101606 A1 | 12/2003 |
| WO | WO-2007/096592 A1 | 8/2007 |
| WO | WO 2011/160733 A1 * | 12/2011 |
| WO | WO-2011/160733 A1 | 12/2011 |
| WO | WO-2011/161229 A1 | 12/2011 |
| WO | WO-2012/107323 A1 | 8/2012 |
| WO | WO-2013/092375 A1 | 6/2013 |

OTHER PUBLICATIONS

Extended European Search Report for EP Patent Application No. 14192185.8, dated May 20, 2015 (10 pages).
International Preliminary Report on Patentability for PCT Patent Application No. PCT/EP2015/074825, dated May 18, 2017 (7 pages).
International Search Report for PCT Patent Application No. PCT/EP2015/074825, dated Jan. 12, 2016 (10 pages).
Schrader, K., "Grundlagen und Rezepturen der Kosmetik," *Verlag Hüthig*, Heidelberg, 2nd Edition, 1989, pp. 319-355.
Yanhong, M., et al., "The Effect of Different Soft Segments on the Formation and Properties of Binary Core Microencapsulated Phase Change Materials with Polyurea/Polyurethane Double Shell." *Journal of Colloid and interface Science* 392 (2013), pp. 407-414.

* cited by examiner

*Primary Examiner* — Blessing M Fubara
(74) *Attorney, Agent, or Firm* — Marshall, Gerstein & Borun LLP

(57) ABSTRACT

The application describes a process for the preparation of microcapsules, wherein the microcapsules have a volume average diameter d of 15 to 90 µm and a percentage of the shell weight of 3 to 40%, with reference to the total weight of capsules, wherein the shell of the microcapsules comprises at least one polyurea and the core comprises at least one lipophilic component, comprising the step of adding hydroxyalkylcellulose to a dispersion of polyurea microcapsules, microcapsules and their uses.

19 Claims, No Drawings

PROCESS FOR PREPARING MICROCAPSULES HAVING A POLYUREA SHELL AND A LIPOPHILIC CORE MATERIAL

CROSS-REFERENCE TO RELATED APPLICATIONS

This is the U.S. national stage application of PCT/EP2015/074825, filed Oct. 27, 2015, which claims the benefit of European Patent Application No. 14192185.8, filed Nov. 7, 2014.

BACKGROUND OF THE INVENTION

The present invention relates to process for preparing microcapsules having a polyurea shell and a lipophilic core material, a dispersion of those microcapsules in an aqueous medium and the use thereof.

STATE OF THE ART

Microcapsules are spherical objects which consist of a core and a wall material surrounding the core, wherein the core in principal can be a solid, liquid or gaseous component which is surrounded by the solid wall material. For many applications the wall is formed by a polymer material. Microcapsules usually have a volume average diameter from 1 to 1000 µm.

A multitude of shell materials is known for producing the wall of microcapsules. The shell can consist either of natural, semisynthetic or synthetic materials. Natural shell materials are, for example, gum arabic, agar agar, agarose, maltodextrins, alginic acid or its salts, e.g. sodium alginate or calcium alginate, fats and fatty acids, cetyl alcohol, collagen, chitosan, lecithins, gelatin, albumin, shellac, polysaccharides, such as starch or dextran, polypeptides, protein hydrolyzates, sucrose and waxes. Semisynthetic shell materials are inter alia chemically modified celluloses, in particular cellulose esters and cellulose ethers, e.g. cellulose acetate, ethyl cellulose, hydroxypropylcellulose, hydroxypropylmethylcellulose and carboxy-methylcellulose, and also starch derivatives, in particular starch ethers and starch esters. Synthetic shell materials are, for example, polymers, such as polyacrylates, polyamides, polyvinyl alcohol, polyvinylpyrrolidone or polyurea.

Depending on the type of shell material and the production process, microcapsules are formed in each case with different properties, such as diameter, size distribution and physical and/or chemical properties.

Polyurea core-shell microcapsules obtained by reaction of two diisocyanates and a polyamine are well known in the art, for example from WO 2011/161229 or WO 2011/160733. According to WO 2011/161229 or WO 2011/160733 the polyurea microcapsules are prepared in presence of polyvinylpyrrolidone (PVP) as a protective colloid.

WO 2012/107323 discloses polyurea microcapsules having a polyurea shell comprising the reaction product of a polyisocyanate with guanazole and an amino acid in presence of anionic stabilizers or surfactants like anionic polyvinyl alcohol, such as Mowiol® KL-506 sold by Kuraray.

EP-B-0 537 467 describes microcapsules prepared from isocyanates which are containing polyethylenoxide groups, in the presence of stabilizers like polyvinyl alcohol, e.g. partially or totally saponified polyvinyl acetate.

According to WO 2007/096592, microencapsulation can take place in an oil phase which is emulsified in a continuous aqueous phase, generally stabilized by a surfactant system like polyvinyl alcohols or carboxylated and sulphonated derivatives thereof.

These is a continuing demand for delivery systems that allows controlled delivery of hydrophilic compounds under defined application conditions. This comprises e.g. the delivery of a cosmetically or pharmaceutically active component to a person or animal.

Thus, several techniques are used to provide stable dosage forms that allow a controlled release of these additives. Encapsulated lipophilic components which are different from perfume, are manufactured in the form of a dispersion of microcapsules in an aqueous medium. It is important to ensure that the distribution of the lipophilic component-containing capsules in a dispersion is controlled in order that the microcapsules do not phase separate from the aqueous dispersing medium and cream, sediment or coagulate. In order to properly disperse and suspend microcapsules within an aqueous dispersing medium, to provide a composition with long time stability, dispersing aids are commonly employed in the manufacture of those dispersions.

A wide variety of dispersing aids are known in the art and include polysaccharides, pectine, alginate, arabinogalactan, carageenan, gellan gum, xanthan gum, guar gum, acrylates/acrylic polymers, starches, water-swellable clays, acrylate/aminoacrylate copolymers, and mixtures thereof, maltodextrin; natural gums, such as alginate esters; gelatine, protein hydrolysates and their quaternized forms; synthetic polymers and copolymers, such as poly(vinyl pyrrolidone-co-vinyl acetate), poly(vinyl alcohol-co-vinyl acetate), poly (maleic acid), poly(alkyleneoxide), poly(vinylmethylether), poly(vinylether-co-maleic anhydride), and the like, as well as poly-(ethyleneimine), poly((meth)acrylamide), poly(alkyleneoxide-co-dimethylsiloxane), poly(amino dimethylsiloxane), and the like.

Despite the variety of dispersing aids that are available for use, the selection of the appropriate dispersing aid will depend on a number of factors, including the capsule shell chemistry, its morphology, its size and density, as well as the composition of the aqueous dispersing media, such as its pH and electrolyte content, all of which will be influenced to a certain extent by the encapsulation process conditions.

Indeed, it proved difficult to prepare in a reliable and reproducible way encapsulated lipophilic components which are different from perfume, comprising polyurea microcapsules in the form of aqueous dispersion. Phase separation as well as viscosity of the dispersion was difficult to control. If the visosity of the dispersion is too high, often excessive processing forces need to be employed which in turn can damage the microcapsules. Furthermore, highly viscous dispersion can be difficult to handle and can lead to difficulties when incorporating the lipophilic components into consumer products.

It is an object of the present invention to provide a process for microcapsules with tailord properties. In particular, it is an object of the present invention to provide a process for microcapsules, wherein the size of the micropasules can be controlled in a wide range and that are capable releasing an encapsulated ingredient under controlled conditions. Especially, it is an object of the present invention to provide a process for microcapsules which have at least one encalspulated lipophilic component with the proviso that the core does not contain a fragrance, wherein the microcapsules have enhanced stability against leacking-out of the lipophilic components from the capsules. Additionally, it is very important to provide microcapsule dispersions with a high stability against phase separation in view of a good storage stability for their use. Further, it is an object of the present invention to provide stable microcapsule dispersions for the use as or in a personal care composition, as or in a composition used for industrial or institutional or hospital desinfection, as or in a material protection composition, as or in a pharmaceutical composition, as or in a plant protection composition, as or in home care products.

All in all, it was an object of the present invention to prepare microcapsules with tailored properties and to provide these microcapsules in form of a dispersion with good phase separation properties.

Surprisingly, these objects could be achieved by a process for the preparation of microcapsules, wherein the microcapsules have a volume average diameter of 15 to 90 µm and a percentage of the shell weight of 3 to 40%, with reference to the total weight of capsules, wherein the shell of the microcapsules comprises at least one polyurea and the core comprises at least one lipophilic component with the proviso that the core does not contain a fragrance comprising the steps of:
  providing an aqueous solution comprising at least one protective colloid,
  providing at least one polyisocyanate and at least one lipophilic component,
  mixing the aqueous solution, the polyisocyanate and the lipophilic components to form an emulsion,
  adding an aqueous solution containing at least one polyfunctional amine to initiate the polyaddition reaction,
  forming a dispersion of microcapsules by heating the obtained mixture to a temperature of at least 50° C. until microcapsules are formed and
  adding hydroxyalkylcellulose to the obtained dispersion.

It has further surprisingly been found that the ratio of the shell weight to the volume average diameter of the microcapsules is a suitable parameter to select microcapsules having desired release properties depending on the mechanical stress applied to the microcapsules. The mechanical stress applied to the capsules is a typical parameter for each field of application.

It has further surprisingly been found that the hydroxyalkylcellulose is a suitable stabilizing agent for these kind of microcapsules.

SUMMERY OF THE INVENTION

The present invention relates to a process for the preparation of microcapsules, wherein the microcapsules have a volume average diameter d 50 of 15 to 90 µm and a percentage of the shell weight of 3 to 40%, with reference to the total weight of capsules, wherein the shell of the microcapsules comprises at least one polyurea and the core comprises at least one lipophilic component with the proviso that the core does not contain a fragrance, comprising the steps of:
  a) providing a premix (I) comprising at least one protective colloid different from hydroxyalkyl-cellulose in an aqueous solution,
  b) providing a premix (II) comprising at least one polyisocyanate and the at least one lipophilic component,
  c) mixing premix (I) and premix (II) until an emulsion (III) is formed,
  d) adding an aqueous solution (IV) containing at least one polyfunctional amine to the emulsion formed in step c),
  e) forming a dispersion of microcapsules by heating the mixture obtained in step d) to a temperature of at least 50° C. until microcapsules are formed, and
  f) adding hydroxyalkylcelluloses to the dispersion obtained in step e)

The present invention further relates to microcapsules obtained by the process according to the invention.

The present invention further relates to the use of a microcapsules obtained by the process according to the invention in
  a personal care composition or
  a home care composition or
  a composition used for industrial or institutional or hospital applications or
  a material protection composition or
  a pharmaceutical composition or
  a plant protection composition.

The present invention further relates to the microcapsules obtained by the process according to the invention are used in
  a cosmetic composition or
  a hygiene composition or
  a composition for industrial or institutional or hospital cleaning or disinfection,
  laundry detergents,
  fabric softeners,
  dishwashing liquids,
  household cleaners or
  industrial cleaners.

The present invention further relates to the microcapsules obtained by the process according to the invention which are used for finishing of textiles, papers or nonwovens.

The present invention relates to a process for identifying microcapsules wherein the shell of the microcapsules comprises at least one polyurea and the core comprises one or more lipophilic components which are different from perfume, having good release properties, wherein a ratio of the shell weight to the volume average diameter of the capsules of at most 0.7 µm$^{-1}$.

DETAILED DESCRIPTION OF THE INVENTION

The core of the microcapsule composition according to the invention does not contain any fragrance. This holds also for a mixture of fragrances or formulation of fragrances denoted as "perfume" or "scent".

The volume average particle size is measured by light scattering measurements using a Malvern 2000S instrument and the Mie scattering theory. The principle of the Mie theory and how light scattering can be used to measure capsule size can be found, for example in H. C. van de Hulst, Light scattering by small particles, Dover, N.Y., 1981. The primary information provided by static light scattering is the angular dependence of the light scattering intensity which in turn is linked to the size and shape of the capsules. However, in a standard operation method, the size of a sphere having a size equivalent to the size of the diffracting object, whatever the shape of this object is, is calculated by the Malvern proprietary software provided with the apparatus. In case of polydisperse samples, the angular dependence of the overall scattering intensity contains information about the size distribution in the sample. The output is a histogram representing the total volume of capsules belonging to a given size class as a function of the capsule size, whereas an arbitrary number of 50 size classes is typically chosen.

Experimentally, a few drops of the dispersion containing about 10% of capsules are added to a circulating stream of degased water flowing through a scattering cell. The angular distribution of the scattering intensity is measured and analyzed by Malvern proprietary software to provide the average size and size-distribution of the capsules present in the sample. In the context of the present invention, the percentiles D 10, D 50 and D 90 are used as characteristics of the particle size distribution, whereas D 50 corresponds to the median (=average) of the distribution. In the present invention the term "particle size" means "volume particle size".

Young's Module (E-Modulus)

The elastic modulus of microcapsule membranes are studied by using an Atomic Force Microscope (AFM). The working principle of atomic force microscopy is based on a scanning probe tip, which interacts with an underlying surface with low forces. A laser is focused on the cantilever tip and the reflected laser beam is recorded by a photodiode. The photodiode detects cantilever deformations. The AFM probe tip is connected to a piezoelectric transducer in order to move the tip with respect to the sample. Hence a topographically image of the sample surface with nanometer resolution can be obtained. In general the AFM is operated in the so called Tapping Mode. Thereby the AFM cantilever tip is driven by an oscillating actuator at a set frequency close to the resonance frequency of the cantilever and feedback-loop keeps the oscillation amplitude constant. During each oscillation the tip strikes the sample surface. Tip-sample interactions can lead to a phase angle between the external force signal and the cantilever deflection signal. The so called phase shift provides information about the material properties of the sample surface. However these data are not quantitative.

In order to get quantitative mechanical information of the microcapsule surface the Peak-Force Quantitative Nano-Mechanics mode (PF-QNM) is used. Here the AFM cantilever system is oscillating at a much lower frequency compared to the resonance frequency of the AFM cantilever. For each oscillation cycle of the cantilever-tip system a complete Force-Distance curve is recorded and analyzed. Therefore a full data set including topography, elasticity, plasticity, and work of adhesion of a given surface can be studied. A detailed description of this method is given in the U.S. Pat. No. 8,650,660 B2 "Method and apparatus of using peak force tapping mode to measure physical properties of a sample".

Nominal Rupture Stress (NRS)

The burst force of microcapsules is investigated using a micro-manipulation method. Microcapsules are diluted in distilled water and cast on a mica plate and dried at room temperature (24±1° C.). The coated mica plate is then placed on a positioning stage of the micro-manipulation set-up. The set-up includes a tip (diameter of the tip apex is in the μm-range), perpendicular to the positioning stage which is connected to an actuation-based force transducers allowing simultaneous force and displacement measurements. An additional optical camera allows imaging and analyzing the cross-section of individual microcapsules.

The measurement of the burst force is done by compressing individual microcapsules between tip and mica surface and simultaneously recording the imposed load and tip displacement. Typically, the microcapsules burst at a critical load at the time of compression. Images of individual microcapsules are taken before and after each compression test in order to verify bursting. From the force-displacement curves the load and microcapsule deformation at bursting are obtained.

The load at bursting is measured in mN (Millinewton) and the microcapsule diameter is measured in μm (Micrometer). For each type of microcapsule more than 45 individual measurements were performed. The nominal rupture stress (NRS) is defined as the load at bursting divided by the projected area of the microcapsule.

A "stable dispersion" in the sense of the present invention denotes a dispersion of polyurea microcapsules which, upon visible inspection, shows no sign of phase separation, such as creaming, settling, precipitation or coagulation when stored for a period of two weeks at a temperature of 50° C.

The term "aqueous dispersion" in the sense of the invention denotes water and mixtures of water with at least one at least partly water-miscible organic solvent. Suitable organic solvents are e.g. $C_1$-$C_4$-alkanols. The $C_1$-$C_4$-alkanols are preferably selected from among methanol, ethanol, n-propanol, isopropanol and n-butanol. Mixtures of at least one $C_1$-$C_4$-alkanol with water preferably comprise from 0.1 to 99.9% by weight, particularly preferably from 0.2 to 50% by weight, in particular from 0.3 to 10% by weight of at least one $C_1$-$C_4$-alkanol, based on the total weight of the mixture. In a special embodiment the aqueous dispersion consists of water.

Within the context of the present invention, the microcapsules have a shell that is prepared by reacting at least one polyisocyanate with at least one polyfunctional amine and optionally further components capable of being incorporated into the shell. In a special embodiment, the shell is the reaction product of at least two different polyisocyanates with at least one polyfunctional amine. The reaction is a polycondensation between the isocyanate groups and the amine groups and optional further groups, capable of reacting with NCO groups, which leads to the formation of polyurea linkages. The polyfunctional amine may in addition to at least one primary or secondary amine contain at least one further group, capable of reacting with NCO groups, e.g. at least one OH group. Further components, capable of being incorporated into the shell are in principle all compounds which contain at least one active hydrogen atom per molecule. Reaction of NCO groups with amine groups leads to the formation of urea groups. Reaction of NCO groups with OH groups leads to the formation of urethane groups. Compounds containing only one active hydrogen atom per molecule lead to a termination of the polymer chain and can be employed as regulators. Compounds containing more than two active hydrogen atoms per molecule lead to the formation of branched polyureas.

The compounds which contain at least one active hydrogen atom per molecule are usually employed in a molar excess of active hydrogen atoms relative to the NCO groups of the polyisocyanate. The amount of polyfunctional amines which is introduced is usually in a molar excess, relative to the stoichiometric amount needed to convert the free isocyanate groups. Suitable polyisocyanates, polyfunctional amines, optional components that take part in the polyaddition reaction, lipophilic components, protective colloids, stabilizing agent and further additives, are mentioned below.

In one preferred embodiment, the process is carried out as follows:
  a) providing a premix (I) comprising at least one protective colloid different from hydroxyalkylcellulose in an aqueous solution,
  b) providing a further premix (II) comprising at least one lipophilic component and a first polyisocyanate (A), c) mixing premix (I) and premix (II) until an emulsion is formed and adding a second polyisocyanate (B) to the emulsion obtained in step c),
d) adding an aqueous solution (IV) containing at least one polyfunctional amine to the emulsion formed in step c),
e) forming a dispersion of microcapsules by heating the mixture obtained in step d) to a temperature of at least 50° C. until microcapsules are formed and
f) adding hydroxyalkylcellulose to the dispersion obtained in step e).

In one preferred embodiment, the process is carried out as follows:
a) providing a premix (I) comprising at least one protective colloid different from hydroxyalkylcellulose in an aqueous solution and adjusting the pH in a range of from 5 to 12,
b) providing a further premix (II) comprising at least one lipophilic component and a first polyisocyanate (A),
c) mixing premix (I) and premix (II) until an emulsion is formed and adding a second polyisocyanate (B) to the emulsion obtained in step c) and adjusting the pH of the resulting emulsion in a range of from 5 to 10,
d) adding an aqueous solution (IV) containing at least one polyfunctional amine to the emulsion formed in step c),
e) forming a dispersion of microcapsules by heating the mixture obtained in step d) to a temperature of at least 50° C. until microcapsules are formed and
f) adding hydroxyalkylcellulose to the dispersion obtained in step e).

Step a)

Premix (I) provided in step a) contains an aqueous solvent. Suitable solvents are water and mixtures of water with at least one water-miscible organic solvent. Suitable water-miscible organic solvent are mentioned above. Preferably, the solvent is essentially water.

The aqueous solution provided in step a) comprises at least one protective colloid. The protective colloid provided in step a) is preferably different from hydroxyalkylcellulose.

During the reaction between the polyisocyanates and the polyfunctional amines, a protective colloid may be present. Protective colloids are polymer systems which, in suspensions or dispersions, prevent a clumping together (agglomeration, coagulation, flocculation) of the emulsified, suspended or dispersed components. During solvation, protective colloids bind large amounts of water and in aqueous solutions produce high viscosities depending on the concentration. Within the context of the process described herein, the protective colloid may also have emulsifying properties. The aqueous protective colloid solution is likewise preferably prepared with stirring.

Preferably, premix (I) comprises at least one protective colloid selected from polyvinylpyrrolidones, polyvinyl alcohols, maleic-vinyl copolymers, sodium lignosulfonates, maleic anhydride/styrene copolymers, ethylene/maleic anhydride copolymers, copolymers of ethylene oxide, propylene oxide and ethylenediamine, fatty acid esters of polyethoxylated sorbitol, sodium dodecylsulfate and mixtures thereof. More preferably, premix (I) comprises at least one protective colloid selected from polyvinylpyrrolidones, polyvinyl alcohols and mixtures thereof. Polyvinylpyrrolidones are particularly preferred.

Standard commercial polyvinylpyrrolidones have molar masses in the range from ca. 2500-750000 g/mol which are characterized with K values and have—depending on the K value—glass transition temperatures from 130 to 175° C. They are supplied as white, hygroscopic powders or as aqueous solutions.

The polyvinylpyrrolidones used in premix (I) preferably have a K value (determined at 25° C. in a 1% by weight aqueous or ethanolic solution) of at least 10, particularly preferably of at least 20, more preferably of at least 80. Determination of the K value is described in H. Fikentscher "Systematik der Cellulosen auf Grund ihrer Viskosität in Lösung", Cellulose-Chemie 13 (1932), 58-64 and 71-74, and Encyclopedia of Chemical Technology, Vol. 21, $2^{nd}$ edition, 427-428 (1970).

Suitable commercially available polyvinylpyrrolidones are the Kollidon® trademarks from BASF SE. Preferred polyvinylpyrrolidones useful in the practice of the present invention are available in three grades: Kollidon®® 25 (BASF Corporation), Kollidon®® 90 (BASF Corporation), and Kollidon®® CI-M (BASF Corporation). Kollidon®® 25 has a weight average molecular weight of 28000-34000. Kollidon®® 90 has a molecular weight average of 1000000-1500000. Further commercially available polyvinylpyrrolidones are Kollidon® 12 which has a weight average molecular weight of 2000-3000, Kollidon® 17 which has a weight average molecular weight of 7000-11000 and Kollidon® 30 which has a weight average molecular weight of 44000-54000.

Particular protective colloids include polyvinyl alcohol copolymers having a degree of hydrolysis in the range of 85 to 99.9%. As used herein, the term "polyvinyl alcohol copolymer" means a polymer of vinyl alcohol/vinyl acetate with comonomers.

It is known that polyvinyl alcohol is produced by hydrolysis (deacetylation) of polyvinylacetate, whereby ester groups of polyvinyl acetate are hydrolysed into hydroxyl groups, thus forming polyvinyl alcohol.

The degree of hydrolysis reflects the percentage of groups that are converted by hydrolysis. The term "polyvinyl alcohol", qualified by a degree of hydrolysis, means therefore a vinyl polymer containing both ester and hydroxyl groups.

In a particular embodiment of the invention, copolymers of polyvinyl alcohol with a degree of hydrolysis in the range of 85 to 99.9%, more particularly 85 to 95% may be used as protective colloids.

The degree of hydrolysis can be determined by techniques well known in the art, for example, according to DIN 53401.

The polyvinyl alcohol copolymers contain addition comonomers, that is, comonomers that are polymerized with a vinyl ester in a first step, followed by hydrolysis of the ester groups to form the copolymer of polyvinyl alcohol in a second step. Copolymers may be formed by radical polymerization of vinyl acetate and comonomers in a manner known per se.

Polyvinyl alcohol copolymers may contain unsaturated hydrocarbons as comonomers. These hydrocarbons may be modified with charged or non-charged functional groups. Particular comonomers include, but are not limited to:
  unsaturated hydrocarbons with 2 or 3 carbon atoms and no functional groups, e.g. ethylene,
  unsaturated hydrocarbons having 2 to 6 carbon atoms and non-charged functional groups, such as hydroxyl groups, e.g. buten-1,4-diol,
  unsaturated hydrocarbons having anionic groups, such as carboxyl, and/or sulphonic acid groups,
  unsaturated hydrocarbons having cationic groups, such as quaternary ammonium groups.

Particular copolymers of polyvinyl alcohol include those having a degree of hydrolysis of 85 to 99.9%, and more particularly 85 to 95%; and which contain 0.1 to 30 mol % of comonomers containing anionic groups as mentioned above; or 0.1 to 30 mol % of comonomers containing cationic groups as mentioned above or 0.1 to 30 mol % of comonomers with unsaturated hydrocarbons having 2 to 6 carbon atoms and non-charged functional groups, especially two hydroxyl groups, wherein mol % is based on the vinyl acetate/comonomer polymerization mixture.

Suitable copolymers of polyvinyl alcohol and comonomers having 1,2 diol structures are described in EP 2 426 172 and EP 2 648 211 which are herein incorporated by reference.

Particularly preferred polyvinyl alcohols are the G-polymer type available from Nichigo.

The following protective colloids are particularly useful in the preparation of polyurea capsule compositions of the present invention:

Anionic polyvinyl alcohol copolymers with a degree of hydrolysis of greater than 80%, preferably 85.0% to 99.5%, and a viscosity of 2 mPas to 70 mPas (DP 100-6000), for example K-polymer KL-318 from Kuraray (viscosity 20 to 30 mPas, hydrolysis 85.0 to 90.0%); Gohsenal T-350 from Nippon Gohesi (viscosity 27 to 33 mPas, hydrolysis 93.0 to 95.0%); Gohseran L-3266 from Nippon Gohsei (viscosity 2.3 to 2.7 mPas, hydrolysis 86.5 to 89.0%);

Non-charged polyvinyl alcohol copolymers with a degree of hydrolysis of greater that 80%, preferably 85.0 to 99.5%, and a viscosity of 2 mPas to 70 mPas (DP 100-6000), for example G-polymer OKS-8041 from Nippon Gohsei (viscosity 2.8 to 3.3 mPas, hydrolysis 88.0 to 90.0%), G-polymer AZF-8035 from Nippon Gohsei (viscosity 2.8 to 3.3 mPas, hydrolysis 98.5 to 99.5%) and Cationic polyvinyl alcohol copolymers with a degree of hydrolysis of greater than 80% and more particularly 85.0 to 99.5%, and a viscosity of 2 mPas to 70 mPas (DP 100-6000), for example Gohsefimer K-210 from Nippon Gohsei (viscosity 18.0 to 22.0 mPas, hydrolysis 85.5 to 88.0%).

The prorective colloid can be, but does not have to be, a constituent of the capsule shell.

The protective colloid may be, but does not have to be, a constituent of the capsule shell with amounts from 0.1 to at most 15% by weight, but preferably in the range from 1 to 5% by weight and in particular from 1.5 to 3% by weight, based on the weight of the capsules, being possible here.

Combinations of two or more different protective colloids may also be employed in the present invention.

In a further preferred embodiment, the protective colloid employed in step a) comprises or consists of at least one polyvinylpyrrolidone.

Premix (I) may also contain at least one emulsifier. Emulsifiers include non-ionic, cationic, anionic and zwitterionic surfactants.

Suitable non-ionic surfactants are selected from the group consisting of products of the addition of 2 to 30 mol ethylene oxide and/or 0 to 5 mol propylene oxide onto linear $C_{6-22}$ fatty alcohols, onto $C_{12-22}$ fatty acids, onto alkyl phenols containing 8 to 15 carbon atoms in the alkyl group and onto alkylamines containing 8 to 22 carbon atoms in the alkyl group; alkyl oligoglycosides containing 8 to 22 carbon atoms in the alkyl group and ethoxylated analogs thereof; addition products of 1 to 15 mol ethylene oxide onto castor oil and/or hydrogenated castor oil; addition products of 15 to 60 mol ethylene oxide onto castor oil and/or hydrogenated castor oil; partial esters of glycerol and/or sorbitan with unsaturated, linear or saturated branched fatty acids containing 12 to 22 carbon atoms and/or hydroxycarboxylic acids containing 3 to 18 carbon atoms and addition products thereof onto 1 to 30 mol ethylene oxide; partial esters of polyglycerol (average degree of self-condensation 2 to 8), polyethylene glycol (molecular weight 400 to 5,000), trimethylolpropane, pentaerythritol, sugar alcohols (for example sorbitol), alkyl glucosides (for example methyl glucoside, butyl glucoside, lauryl glucoside) and polyglucosides (for example cellulose) with saturated and/or unsaturated, linear or branched fatty acids containing 12 to 22 carbon atoms and/or hydroxycarboxylic acids containing 3 to 18 carbon atoms and addition products thereof onto 1 to 30 mol ethylene oxide; mixed esters of pentaerythritol, fatty acids, citric acid and fatty alcohol and/or mixed esters of fatty acids containing 6 to 22 carbon atoms, methyl glucose and polyols, preferably glycerol or polyglycerol, mono-, di- and trialkyl phosphates and mono-, di- and/or tri-PEG-alkyl phosphates and salts thereof, wool wax alcohols, polysiloxane/polyalkyl/polyether copolymers and corresponding derivatives, block copolymers, for example Polyethyleneglycol-30 Dipolyhydroxystearate; polymer emulsifiers, for example Pemulen types (TR-1, TR-2) of Goodrich; polyalkylene glycols and glycerol carbonate and ethylene oxide addition products.

Step b)

Premix (II) provided in step b) comprises at least one polyisocyanate providing and at least one lipophilic component.

Premix (II) is generally in liquid form. Preferably, premix (II) contains no or only a minor amount of solid components. In the sense of the invention, a minor amount means that the amount of solid components is at the most 5% by weight, preferably at the most 1% by weight, more preferably at the most 0.1% by weight, based on the total weight of premix (II). In particular, premix (II) contains no solid components.

Premix (II) optionally contains at least one organic solvent. An organic solvent is particularly used if the mixture of the employed polyisocyanates and the employed lipophilic components is not liquid under the conditions of process step b).

Lipophilic components are in general components which have only limited solubility in water. This includes hydrophobic components that are liquid under the encapsulation conditions and mixtures of hydrophobic components, wherein the mixture is liquid under the encapsulation conditions. Said mixtures may contain at least one hydrophobic component that is solid, but is solubilized in at least one liquid component.

Premix (II) does not contain a fragrance as hydrophobic component. In the sense of the invention the term perfume or any fragrances as such materials are excluded.

Suitable lipophilic components are mentioned in detail below. In the sense of the invention, the term "lipophilic component" is understood in a broad sense. It encompasses a single lipophilic component, a mixture comprising at least two lipophilic components and a solution of at least one lipophilic solid compound in a liquid lipophilic compound.

The lipophilic components used according to the invention have only a limited solubility in water. The solubility of the lipophilic components in water at 20° C. and 1013 mbar is preferably 10 mg/mL, more preferably 5 mg/mL, in particular 3 mg/mL.

In a special embodiment of the invention, the microcapsules contain substantially no solvent in the core. According to the process of the invention, it is possible to prepare a microcapsule composition, wherein the encapsulated cores are composed entirely of lipophilic components and no solvents. Solvent-free encapsulated lipophilic components may be employed, in particular, when the lipophilic components making up the core material are liquid under the condions used for the preparation of the microcapsules.

Preferably, at least 60% by weight, more preferably at least 70% by weight, in particular at least 80% by weight and especially at least 90% by weight of lipophilic components, based on the total weight of the lipophilic components, have a solubility in water at 20° C. and 1013 mbar of ≤10 mg/mL, particularly ≤5 mg/mL, and more particularly ≤3 mg/mL.

The microcapsules contain one or more lipophilic components. Preferably, the amount of the lipophilic components is in a range of from 5 to 97% by weight, more preferably 10 to 95% by weight, in particular 25 to 93% by weight, based on the total weight of the microcapsules. In a special embodiment, the amount of the lipophilic components is in a range of from 70 to 98% by weight, based on the total weight of the microcapsules.

Preferably, the amount of the lipophilic components is in a range of from 5 to 65% by weight, more preferably 10 to 50% by weight, in particular 20 to 40% by weight, especially 25 to 35% by weight, based on the total weight of the microcapsule composition.

Advantageously, a large amount of lipophilic components can be encapsulated in the microcapsules of the invention despite the relatively low shell weight. Preferably, the ratio of the total weight of the lipophilic components to total weight of the shell material is in a range of from 60% to 95% by weight, more preferably 75% to 80% by weight, and more particularly 80% to 88% by weight.

The core-shell weight ratio may be obtained by weighing an amount of capsules that have been previously washed with water and separated by filtration. The core is then extracted by solvent extraction techniques to give a core weight. The shell weight is obtained from simple mass balance taking into account the initial amount of encapsulating materials in weight %.

Lipophilic components that are used can be various organic substances. In particular, the lipophilic component is selected from active ingredients and auxiliaries for cosmetics (e.g. hair and skin cosmetics), pharmaceuticals, hygiene compositions, detergents, cleaning agents, textile treatment compositions, etc., compositions used for industrial or institutional or hospital applications, material protection compositions or plant protection compositions. Especially, the lipophilic component is selected from active substances and additives for personal care compositions, home care compositions, compositions used for industrial or institutional or hospital applications, material protection compositions, pharmaceutical compositions or plant protection composition.

Active ingredients are substances which generally develop an effect even at low concentration, e.g. a cosmetic effect on skin and/or hair, a pharmacological effect in an organism, a plant protecting effect, a cleaning and/or disinfecting effect, a modification of a textile substance, e.g. a crease-free finishing, and effect substances which impart a certain property to living things or inanimate substrates, for example colors for make-up, mascara, etc.

Preferably, the lipophilic component is selected from oil bodies, UV-filters, organic compounds, biocides, dyes, emollients, vitamins, cosmetically active ingredients, pharmaceutically active ingredients, cosmetically and pharmaceutically acceptable auxiliaries, detergents or mixtures thereof.

A first class of lipophilic components that can be encapsulated are oil bodies.

Preferably, the lipophilic components comprise at least one oil body capable to dissolve the polyisocyanates employed in step b). More preferably, these oil body are capable to dissolve the polyisocyanates without extraneous solvents and/or auxiliaries. Should an oil body not ensure adequate solubility of the polyisocyanates, there is the option of overcoming this disadvantage by using suitable solubility promoters.

The term oil body in the sense of the invention means vegetable oils, modified vegetable oils, synthetic (tri)glycerides, fatty acid alkyl esters, fatty acid alkyl esters based on said $C_6$-$C_{22}$ fatty acids, mineral oils, silicone oils, hydrocarbons, saturated or unsaturated $C_6$-$C_{30}$-fatty acids, aromatic compounds, waxes, polymers, Guerbet alcohols based on fatty alcohols, esters of linear $C_6$-$C_{22}$-fatty acids and mixtures thereof.

Suitable vegetable oils are rape seed oil, sunflower oil, soy oil, olive oil and mixtures thereof.

Modified vegetable oils are alkoxylated sunflower or soy oil and mixtures thereof.

Synthetic (tri)glycerides are technical mixtures of mono, di and triglycerides of $C_6$-$C_{22}$ fatty acids and mixtures thereof. Preferred are caprylic/capric triglyceride. Preferred commercially available caprylic/capric triglyceride are sold by BASF SE under the trade mark Myritol®.

Suitable fatty acid alkyl esters are selected from methyl or ethyl esters of vegetable oils. Preferred commercially available fatty acid alkyl esters sold by BASF SE under the trade marks Agnique® ME 18 RD-F, Agnique® ME 18 SD-F, Agnique® ME 12C-F, Agnique®.

Suitable silicone oils are cyclomethicones or silicon methicone types;

Suitable aliphatic hydrocarbon compounds are straight-chain alkanes or paraffinic hydrocarbons, branched-chain alkanes, unsaturated hydrocarbons, halogenated hydrocarbons, and alicyclic hydrocarbons, such as hexane, cyclohexane, decane, chloroparaffines, fluorinated hydrocarbons, saturated or unsaturated $C_1$-$C_{40}$-hadrocarbons which are branched or linear, e. g. n-tetradecane, n-pentadecane, n-hexadecane, n-heptadecane, n-octadecane, n-nonadecane, n-eicosane, n-heneicosane, n-docosane, n-tricosane, n-tetracosane, n-pentacosane, n-hexacosane, n-heptacosane, n-octacosane, also cyclic hydrocarbons, e.g. cyclohexane, cyclodecane; halogenated hydrocarbons such as chloroparaffines, bromooctadecane, bromo-pentadecane, bromononadecane, bromeicosane, bromodocosane;

Suitable aromatic compounds are benzene, naphthalene, alkylnaphthalenes, biphenyl, o- or n-terphenyl, xylene, toluene dodecylbenzene, $C_1$-$C_{40}$-alkyl-substituted aromatic hydrocarbons, such as dodecylbenzene, tetradecylbenzene, hexadecylbenzene, hexylnaphtalene or decyl-naphtalene;

Suitable saturated or unsaturated $C_6$-$C_{30}$-fatty acids are lauric acid, stearic acid, oleic acid or behenic acid, preferably eutectic mixtures of decanonic acid with for example myristic, palmitic or lauric acid;

Suitable waxes are natural and synthetic waxes, such as montan waxes, montan ester waxes, carnauba waxes, polyethylene wax, oxidized waxes, polyvinyl ether wax, ethylene-vinyl acetate wax or hard waxes obtained from Fischer-Tropsch process;

Suitable polymers are polyethylene, polypropylene, polypropylene glycol, polytetramethylene glycol, polypropylene malonate, polyneopentyl glycol sebacate, polypentane glutarate, polyvinyl myristate, polyvinyl stearate, polyvinyl laurate, polyhexadecyl methacrylate, polyoctadecyl methacrylate, polyesters produced by polycondensation of glycols (or their derivatives) with diacids (or their derivatives), and copolymers, such as polyacrylate or poly(meth)acrylate with alkyl hydrocarbon side chain or with polyethylene glycol side chain and copolymers including polyethylene, polypropylene, polypropylene glycol, or polytetramethylene glycol;

Suitable Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols, linear or branched, symmetrical or asymmetrical dialkyl ethers having 6 to 22 carbon atoms per alkyl group, such as, for example, dicaprylyl ether, ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils; and mixtures of these substances.

Preferred oils are cosmetical acceptable oils like caprylic/capric triglyceride, myristyl myristate, cetyl oleate.

Within the context of the present invention, preferred oil bodies are Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

Also preferred oil bodies are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, linear or branched $C_6$-$C_{22}$-fatty alcohols, in particular dioctyl malates, esters of linear and/or branched fatty acids with polyhydric alcohols (such as e.g. propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as e.g. dicaprylyl carbonate (Cetiol® ™ CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® ™ TN), linear or branched, symmetrical or asymmetrical dialkyl ethers having 6 to 22 carbon atoms per alkyl group, such as e.g. dicaprylyl ether (Cetiol® ™ OE), ring-opening products of epoxidized fatty acid esters with polyols, silicone oils (cyclomethicones, silicon methicone types etc.) and/or aliphatic or naphthenic hydrocarbons, such as e.g. squalane, squalene or dialkylcyclohexanes.

A further class of lipophilic components that can be encapsulated are UV filters.

Preferably, the lipophilic components comprise at least one UV filters capable to dissolve the polyisocyanates employed in step b). More preferably, these UV-filters are capable to dissolve the polyisocyanates without extraneous solvents and/or auxiliaries. Should an UV filter not ensure adequate solubility of the polyisocyanates, there is the option of overcoming this disadvantage by using suitable solubility promoters.

Typical lipophilic UV filters are UV-A filters, UV-B filters or broad-spectrum UV NB filters are, for example, 3-benzylidenecamphor or 3-benzylidenenorcamphor and derivatives thereof, e.g. 3-(4-methylbenzylidene)-camphor, 3-(4'-trimethylammonium)benzylidenebornan-2-one methylsulfate (Mexoryl SO), 3,3'-(1,4-phenylenedimethine)bis(7,7-dimethyl-2-oxobicycle-[2.2.1]heptane-1-methanesulfonic acid) and salts (Mexoryl SX), 3-(4'-sulfo)benzylidenebornan-2-one and salts (Mexoryl SL), polymer of N-{(2 and 4)-[2-oxoborn-3-ylidene)methyl}benzyl]acrylamide (Mexoryl SW), 2-(2H-benzotriazol-2-yl)-4-methyl-6-(2-methyl-3-(1,3,3,3-tetramethyl-1-(trimethylsilyloxy)di-siloxanyl)propyl)phenol (Mexoryl SL), 4-aminobenzoic acid derivatives, preferably 2-ethylhexyl 4-(dimethylamino)benzoate, 2-octyl 4-(dimethylamino)benzoate and amyl 4-(dimethyl-amino) benzoate; esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene); esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably di-2-ethylhexyl 4-methoxybenzmalonate; triazine derivatives, such as e.g. 2,4,6-trianilino(p-carbo-2'-ethyl-1'-hexyloxy)-1,3,5-triazine and 2,4,6-tris[p-(2-ethylhexyloxycarbonyl)anilino]-1,3,5-triazine (Uvinul T 150) or bis(2-ethylhexyl) 4,4'-[(6-[4-((1,1-dimethylethyl)aminocarbonyl)phenylamino]-1,3,5-triazine-2,4-dil)diimino]bisbenzoate (Uvasorb® HEB); 2,2-(methylenebis(6-(2H-benzotriazol-2-yl)-4-(1,1,3,3-tetramethylbutyl)phenol (Tinosorb® M); 2,4-bis[4-(2-ethylhexyloxy)-2-hydroxy-phenyl]-6-(4-methoxyphenyl)-1,3,5-triazine (Tinosorb® S); propane-1,3-diones, such as e.g. 1-(4-tert-butylphenyl)-3-(4'-methoxyphenyl) propane-1,3-dione; ketotricyclo(5.2.1.0)decane derivatives, dimethicodiethyl benzalmalonate (Parsol® SLX).

A further class of lipophilic components that can be encapsulated are biocides.

Preferably, the lipophilic components comprise at least one biocide capable to dissolve the polyisocyanates employed in step b). More preferably, these biocides are capable to dissolve the polyisocyanates without extraneous solvents and/or auxiliaries. Should a biocide not ensure adequate solubility of the polyisocyanates, there is the option of overcoming this disadvantage by using suitable solubility promoters.

A biocide is a chemical substance, capable of killing different forms of living organisms used in fields, such as medicine, agriculture, forestry, and mosquito control. Usually, biocides are divided into two sub-groups:
  pesticides which includes fungicides, herbicides, insecticides, algicides, moluscicides, miticides and rodenticides and
  antimicrobials which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests, including insects, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides

A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following species: (3-ethoxy-propyl)mercury bromide, 2-methoxyethylmercury chloride, 2-phenylphenol, 8-hydroxyquinoline sulfate, 8-phenylmercurioxyquinoline, acibenzolar, acylamino acid fungicides, acypetacs, aldimorph, aliphatic nitrogen fungicides, allyl alcohol, amide fungicides, ampropylfos, anilazine, anilide fungicides, antibiotic fungicides, aromatic fungicides, aureofungin, azaconazole, azithiram, azoxystrobin, barium polysulfide, benalaxy,l benalaxyl-M, benodanil, benomyl, benquinox, bentaluron, benthiavalicarb, benzalkonium chloride, benzamacril, benzamide fungicides, benzamorf, benzanilide fungicides, benzimidazole fungicides, benzimidazole precursor fungicides, benzimidazolylcarbamate, benzohydroxamic acid, benzothiazole fungicides, bethoxazin, binapacryl, biphenyl, bitertanol, bithionol, blasticidin-S, Bordeaux mixture, boscalid, bridged diphenyl fungicides, bromuconazole, bupirimate, Burgundy mixture, buthiobate, butylamine, calcium polysulfide, captafol, captan, carbamate fungicides, carbamorph, carbanilate fungicides, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, ciclopirox, climbazole, clotrimazole, conazole fungicides, conazole fungicides (imidazoles), conazole fungicides (triazoles), copper(II) acetate, copper(II) carbonate, basic, copper fungicides, copper hydroxide, copper naphthenate, copper oleate, copper oxychloride, copper(II) sulfate, copper sulfate, basic, copper zinc chromate, cresol, cufraneb, cuprobam, cuprous oxide, cyazofamid, cyclafuramid, cyclic dithiocarbamate fungicides, cycloheximide, cyflufenamid, cymoxanil, cypendazole, cyproconazole, cyprodinil, dazomet, DBCP, debacarb, decafentin, dehydroacetic acid, dicarboximide fungicides, dichlofluanid, dichlone, dichlorophen, dichlorophenyl, dicarboximide fungicides, dichlozoline, diclobutrazol, diclocymet, diclomezine, dicloran, diethofencarb, diethyl pyrocarbonate, difenoconazole, diflumetorim, dimethirimol, dimethomorph, dimoxystrobin, diniconazole, dinitrophenol fungicides, dinobuton, dinocap, dinocton, dinopenton, dinosulfon, dinoterbon, diphenylamine, dipyrithione, disulfiram, ditalimfos, dithianon, dithiocarbamate fungicides, DNOC, dodemorph, dodicin, dodine, DONATODINE, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, ferbam, ferimzone, fluazinam, fludioxonil, flumetover, flumorph, fluopicolide, fluoroimide, fluotrimazole, fluoxastrobin, fluquinconazole, flusilazole, flusulfamide, flutolanil, flutriafol, folpet, formaldehyde, fosetyl, fuberidazole, furalaxyl, furametpyr, furamide fungicides, furanilide fungicides, furcarbanil, furconazole, furconazole-cis, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hymexazol, imazalil, imibenconazole, imidazole fungicides, iminoctadine, inorganic fungicides, inorganic mercury fungicides, iodomethane, ipconazole, iprobenfos, iprodione, iprovalicarb, isoprothiolane, isovaledione, kasugamycin, kresoxim-methyl, lime sulphur, mancopper, mancozeb, maneb, mebenil, mecarbinzid, mepanipyrim, mepronil, mercuric chloride, mercuric oxide, mercurous chloride, mercury fungicides, metalaxyl, metalaxyl-M, metam, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, morpholine fungicides, myclobutanil, myclozolin, N-(ethylmercury)-p-toluenesulphonanilide, nabam, natamycin, nitrostyrene, nitrothal-isopropyl, nuarimol, OCH, octhilinone, ofurace, organomercury fungicides, organophosphorus fungicides, organotin fungicides, orysastrobin, oxadixyl, oxathiin fungicides, oxazole fungicides, oxine copper, oxpoconazole, oxycarboxin, pefurazoate, penconazole, pencycuron, pentachlorophenol, penthiopyrad, phenylmercuriurea, phenylmercury acetate, phenylmercury chloride, phenylmercury derivative of pyrocatechol, phenylmercury nitrate, phenylmercury salicylate, phenylsulfamide fungicides, phosdiphen, phthalide, phthalimide fungicides, picoxystrobin, piperalin, polycarbamate, polymeric dithiocarbamate fungicides, polyoxins, polyoxorim, polysulfide fungicides, potassium azide, potassium polysulfide, potassium thiocyanate, probenazole, prochloraz, procymidone, propamocarb, propiconazole, propineb, proquinazid, prothiocarb, prothioconazole, pyracarbolid, pyraclostrobin, pyrazole fungicides, pyrazophos, pyridine fungicides, pyridinitril, pyrifenox, pyrimethanil, pyrimidine fungicides, pyroquilon, pyroxychlor, pyroxyfur, pyrrole fungicides, quinacetol, quinazamid, quinconazole, quinoline fungicides, quinone fungicides, quinoxaline fungicides, quinoxyfen, quintozene, rabenzazole, salicylanilide, silthiofam, simeconazole, sodium azide, sodium orthophenylphenoxide, sodium pentachlorophenoxide, sodium polysulfide, spiroxamine, streptomycin, strobilurin fungicides, sulfonanilide fungicides, sulfur, sultropen, TCMTB, tebuconazole, tecloftalam, tecnazene, tecoram, tetraconazole, thiabendazole, thiadifluor, thiazole fungicides, thicyofen, thifluzamide, thiocarbamate fungicides, thiochlorfenphim, thiomersal, thiophanate, thiophanate-methyl, thiophene fungicides, thioquinox, thiram, tiadinil, tioxymid, tivedo, tolclofos-methyl, tolnaftate, tolylfluanid, tolylmercury acetate, triadimefon, triadimenol, triamiphos, triarimol, triazbutil, triazine fungicides, triazole fungicides, triazoxide, tributyltin oxide, trichlamide, tricyclazole, tridemorph, trifloxystrobin, triflumizole, triforine, triticonazole, unclassified fungicides, undecylenic acid, uniconazole, urea fungicides, validamycin, valinamide fungicides, vinclozolin, zarilamid, zinc naphthenate, zineb, ziram, zoxamide and their mixtures.

Herbicides

A herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In the following, a number of suitable herbicides are compiled:

2,4-D, a broadleaf herbicide in the phenoxy group used in turf and in no-till field crop production. Now mainly used in a blend with other herbicides that act as synergists, it is the most widely used herbicide in the world, third most commonly used in the United States. It is an example of synthetic auxin (plant hormone).

Atrazine, a triazine herbicide used in corn and sorghum for control of broadleaf weeds and grasses. It is still used because of its low cost and because it works as a synergist when used with other herbicides, it is a photosystem II inhibitor.

Clopyralid, a broadleaf herbicide in the pyridine group, used mainly in turf, rangeland, and for control of noxious thistles. Notorious for its ability to persist in compost. It is another example of synthetic auxin.

Dicamba, a persistent broadleaf herbicide active in the soil, used on turf and field corn. It is another example of synthetic auxin.

Glyphosate, a systemic nonselective (it kills any type of plant) herbicide used in no-till burn-down and for weed control in crops that are genetically modified to resist its effects. It is an example of a EPSPs inhibitor.

Imazapyr, a non-selective herbicide used for the control of a broad range of weeds including terrestrial annual and perennial grasses and broadleaved herbs, woody species, and riparian and emergent aquatic species.

Imazapic, a selective herbicide for both the pre- and post-emergent control of some annual and perennial grasses and some broadleaf weeds. Imazapic kills plants by inhibiting the production of branched chain amino acids (valine, leucine, and isoleucine) which are necessary for protein synthesis and cell growth.

Metoalachlor, a pre-emergent herbicide widely used for control of annual grasses in corn and sorghum; it has largely replaced atrazine for these uses.

Paraquat, a nonselective contact herbicide used for no-till burndown and in aerial destruction of marijuana and coca plantings. More acutely toxic to people than any other herbicide in widespread commercial use.

Picloram, a pyridine herbicide mainly used to control unwanted trees in pastures and edges of fields. It is another synthetic auxin.

Triclopyr.

Insecticides

An insecticide is a pesticide used against insects in all developmental forms. They include ovicides and larvicides used against the eggs and larvae of insects. Insecticides are used in agriculture, medicine, industry and the household. In the following, suitable insecticides are mentioned:

Chlorinated insecticides such as, for example, Camphechlor, DDT, Hexachloro-cyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex and their mixtures;

Organophosphorus compounds, such as, for example, Acephate, Azinphosmethyl, Bensulide, Chlorethoxyfos, Chlorpyrifos, Chlorpyriphosmethyl, Diazinon, Dichlorvos (DDVP), Dicrotophos, Dimethoate, Disulfoton, Ethoprop, Fenamiphos, Fenitrothion, Fenthion, Fosthiazate, Malathion, Methamidophos, Methidathion, Methylparathion, Mevinphos, Naled, Omethoate, Oxydemeton-methyl, Parathion, Phorate, Phosalone, Phosmet, Phostebupirim, Pirimiphosmethyl, Profenofos, Terbufos, Tetrachlorvinphos, Tribufos, Trichlorfon and their mixture;

Carbamates, such as, for example, Aldicarb, Carbofuran, Carbaryl, Methomyl, 2-(1-Methylpropyl)phenyl methylcarbamate and their mixtures;

Pyrethroids, such as, for example, Allethrin, Bifenthrin, Deltamethrin, Permethrin, Resmethrin, Sumithrin, Tetramethrin, Tralomethrin, Transfluthrin and their mixtures;

Plant toxin derived compounds, such as, for example, Derris (rotenone), Pyrethrum, Neem (Azadirachtin), Nicotine, Caffeine and their mixtures.

Rodenticides

Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations and have a delayed effect. In the following, examples for suitable rodenticides are given:

Anticoagulants are defined as chronic (death occurs after 1 to 2 weeks post ingestion of the lethal dose, rarely sooner), single-dose (second generation) or multiple dose (first generation) cumulative rodenticides. Fatal internal bleeding is caused by lethal dose of anticoagulants, such as brodifacoum, coumatetralyl or warfarin. These substances in effective doses are antivitamins K, blocking the enzymes K1-2,3-epoxide-reductase (this enzyme is preferentially blocked by 4-hydroxycoumarin/4-hydroxythiacoumarin derivatives) and K1-quinone-reductase (this enzyme is preferentially blocked by indandione derivatives), depriving the organism of its source of active vitamin K1. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type:

pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001 to 0.005%) and are lethal after single ingestion of bait and are effective also against strains of rodents that have become resistant against first generation anticoagulants; thus, the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02%, etc.) is that the antibiotic/bacteriostatic agent suppresses intestinal/gut symbiotic microflora that represents a source of vitamin K. Thus, the symbiotic bacteria are killed or their metabolism is impaired and the production of vitamin K by them is diminuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e. g., warfarin 0.025-0.05%+cholecalciferol 0.01%. In some countries there are even fixed three-component rodenticides, i.e. anticoagulant+antibiotic+vitamin D, e. g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025 to 0.005% are so toxic that no known resistant strain of rodents exists and even rodents resistant against any other derivatives are reliably exterminated by application of these most toxic anticoagulants.

Vitamin K1 has been suggested and successfully used as an antidote for pets or humans which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them which is an advantage over some older poisons.

Metal phosphides have been used as a means of killing rodents and are considered single-dose fast acting rodenticides (death occurs commonly within 1 to 3 days after single bait ingestion). A bait consisting of food and a phosphide (usually zinc phosphide) is left, where the rodents can eat it. The acid in the digestive system of the rodent reacts with the phosphide to generate the toxic phosphine gas. This method of vermin control has possible use in places, where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness and to get rodents used to feeding in specific areas by offering specific food, especially when eradicating rats) and subsequently applying poisoned bait of the same sort as used for pre-baiting until all consumption of the bait ceases (usually within 2 to 4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75 to 2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin D3) and ergocalciferol (vitamin D2) are used as rodenticides which are toxic to rodents for the same reason that they are beneficial to mammals: they are affecting calcium and phosphate homeostasis in the body. Vitamins D are essential in minute quantities (few lUs per kilogram body weight daily which is only a fraction of a milligram), and like most fat soluble vitamins they are toxic in larger doses as they readily result in the so-called hypervitaminosis which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionized form (mainly monohydrogencarbonate calcium cation, partially bound to plasma proteins, $[CaHCO_3]^+$) which circulates dissolved in the blood plasma, and after ingestion of a lethal dose the free calcium levels are raised sufficiently, so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractibility and excitation propagation between atrias and ventriculas) and bleeding (due to capillary damage) and possibly kidney failure. It is considered to be single-dose or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait, so that a massive hypercalcemic effect can be achieved by a substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075 to 0.1% (e.g. Quintox®, containing 0.075% cholecalciferol) alone, or a combination of calciferol 0.01 to 0.075% with an anticoagulant are marketed.

Miticides, Moluscicides and Nematicides

Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world, but was first cultivated in India since ancient times.

Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds, such as chlorhexidine, glucoprotamine, octenidine dihydrochloride, etc.), strong oxidizers, such as ozone and permanganate solutions, heavy metals and their salts, such as colloidal silver, silver nitrate, mercury chloride, phenyl-mercury salts, copper sulfate, copper oxide-chloride, etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH <1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e. g. Daquin's solution, 0.5% sodium or potassium hypochlorite solution, pH-adjusted to pH 7 to 8, or 0.5 to 1% solution of sodium benzenesulfochloramide (chloramine B)), some iodine preparations, such as iodopovidone in various galenics (ointments, solutions, wound plasters), in the past also Lugol's solution, peroxides as urea perhydrate solutions and pH-buffered 0.1 to 0.25% peracetic acid solutions, alcohols with or without antiseptic additives, used mainly for skin antisepsis, weak organic acids, such as sorbic acid, benzoic acid, lactic acid and salicylic acid some phenolic compounds, such as hexachlorophene, triclosan and Dibromol, and cation-active compounds, such as 0.05 to 0.5% benzalkonium, 0.5 to 4% chlorhexidine, 0.1 to 2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole. The preferred biocides are selected from the group consisting of oxyfluorfen, glyphosate, tebucanozol, desmedipham, phenmedipham, ethofumesat and their mixtures.

A further class of lipophilic components that can be encapsulated are emollients.

Preferably, the lipophilic components comprise at least one emollient capable to dissolve the polyisocyanates employed in step b). More preferably, these emollients are capable to dissolve the polyisocyanates without extraneous solvents and/or auxiliaries. Should an emollient not ensure adequate solubility of the polyisocyanates, there is the option of overcoming this disadvantage by using suitable solubility promoters.

An emollient is a material that softens, soothes, supplies, coats, lubricates, moisturizes, or cleanses the skin. An emollient typically accomplishes several of these objectives such as soothing, moisturizing, and lubricating the skin. Preferred are selected from petroleum-based, fatty acid ester type, alkyl ethoxylate type, fatty acid ester ethoxylates, fatty alcohol type, polysiloxane type, or mixtures thereof.

A further class of lipophilic components that can be encapsulated are dyes.

Preferably, the lipophilic components comprise at least one dye capable to dissolve the polyisocyanates employed in step b). More preferably, these dyes are capable to dissolve the polyisocyanates without extraneous solvents and/or auxiliaries. Should an dye not ensure adequate solubility of the polyisocyanates, there is the option of overcoming this disadvantage by using suitable solubility promoters.

Preferred dyes according to the invention are dyes suitable and approved for cosmetic purposes. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). These dyes are normally used in concentrations of 0.001 to 0.1% by weight, based on the mixture as a whole.

A further class of lipophilic components that can be encapsulated are cosmetically active ingredients.

Preferably, the lipophilic components comprise at least one cosmetically active ingredient capable to dissolve the polyisocyanates employed in step b). More preferably, these cosmetically active ingredients are capable to dissolve the polyisocyanates without extraneous solvents and/or auxiliaries. Should an cosmetically active ingredients not ensure adequate solubility of the polyisocyanates, there is the option of overcoming this disadvantage by using suitable solubility promoters.

Specifically suitable cosmetically compatible oil bodies are described in Karl-Heinz Schrader, Grundlagen and Rezepturen der Kosmetika [Fundamentals and formulations of cosmetics], 2nd edition, Verlag Huthig, Heidelberg, pp. 319-355, to which reference is made here.

Suitable cosmetically active ingredients are, for example, skin and hair pigmentation agents, tanning agents, bleaches, keratin-hardening substances, antimicrobial active ingredients, photofilter active ingredients, repellent active ingredients, hyperemic substances, keratolytic and keratoplastic substances, antidandruff active ingredients, antiphlogistics, keratinizing substances, active ingredients which have an antioxidative effect and/or free-radical scavenging effect, skin-moisturizing or -humectant substances, refatting active ingredients, deodorizing active ingredients, sebostatic active ingredients, plant extracts, antierythimatous or antiallergic active ingredients and mixtures thereof.

Artificially skin-tanning active ingredients which are suitable for tanning of the skin without natural or artificial irradiation with UV rays are, for example, dihydroxyacetone, alloxan and walnut shell extract. Suitable keratin-hardening substances are generally active ingredients as are also used in antiperspirants, such as, for example, potassium aluminum sulfate, aluminum hydroxychloride, aluminum lactate, etc. Antimicrobial active ingredients are used in order to destroy microorganisms and/or to inhibit their growth and thus serve both as preservatives and also as deodorizing substance which reduces the development or the intensity of body odor. These include, for example, customary preservatives known to the person skilled in the art, such as p-hydroxybenzoic acid esters, imidazolidinylurea, formaldehyde, sorbic acid, benzoic acid, salicylic acid, etc. Deodorizing substances of this type are, for example, zinc ricinoleate, triclosan, undecylenic acid alkylolamides, triethyl citrate, chlorhexidine, etc. Suitable photofilter active ingredients are substances which absorb UV rays in the UV-B and/or UV-A region. Suitable UV filters are those specified above. Also suitable are p-aminobenzoic acid esters, cinnamic acid esters, benzophenones, camphor derivatives and pigments which stop UV rays, such as titanium dioxide, talc and zinc oxide. Suitable repellent active ingredients are compounds which are able to deter or drive away certain animals, in particular insects, from people. These include, for example, 2-ethyl-1,3-hexanediol, N,N-diethyl-m-toluamide, etc. Suitable hyperemic substances which stimulate blood flow through the skin, are, for example, essential oils, such as dwarf-pine, lavender, rosemary, juniper berry, horse chestnut extract, birch leaf extract, hay flower extract, ethyl acetate, camphor, menthol, peppermint oil, rosemary extract, eucalyptus oil, etc. Suitable keratolytic and keratoplastic substances are, for example, salicylic acid, calcium thioglycolate, thioglycolic acid and its salts, sulfur, etc. Suitable antidandruff active ingredients are, for example, sulfur, sulfur polyethylene glycol sorbitan monooleate, sulfur ricinol polyethoxylate, zinc pyrithione, aluminum pyrithione, etc. Suitable antiphlogistics which counteract skin irritations, are, for example, allantoin, bisabolol, dragosantol, camille extract, panthenol, etc.

A further class of lipophilic components that can be encapsulated are pharmaceutically ingredients.

Preferably, the lipophilic components comprise at least one pharmaceutically ingredient capable to dissolve the polyisocyanates employed in step b). More preferably, these pharmaceutically ingredients are capable to dissolve the polyisocyanates without extraneous solvents and/or auxiliaries. Should a pharmaceutically ingredient not ensure adequate solubility of the polyisocyanates, there is the option of overcoming this disadvantage by using suitable solubility promoters.

In principle, all pharmaceutical active substances and prodrugs are suitable for the use of the lipophilic components according to the invention. These include benzodiazepines, antihypertensives, vitamins, cytostatics, in particular taxol, anesthetics, neuroleptics, antidepressants, antibiotics, antimycotics, fungicides, chemotherapeutics, urologics, thrombocyte aggregation inhibitors, sulfonamides, spasmolytics, hormones, immunoglobulins, sera, thyroid therapeutic agents, psychopharmacological agents, antiparkinsonians and other antihyperkinetic agents, ophthalmics, neuropathy preparations, calcium metabolism regulators, muscle relaxants, narcotics, antilipemics, hepatic therapeutic agents, coronary agents, cardiacs, immunotherapeutics, regulatory peptides and their inhibitors, hypnotics, sedatives, gynecological agents, antigouts, fibrinolytic agents, enzyme preparations and transport proteins, enzyme inhibitors, emetics, circulation-promoting agents, diuretics, diagnostics, corticoids, cholinergics, bile duct therapeutics, antiasthmatics, broncholytics, beta-receptor blockers, calcium antagonists, ACE inhibitors, antiarteriosclerotics, antiinflammatories, anticoagulants, antihypotensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists and slimming agents. Examples of suitable pharmaceutical active substances are in particular the active substances mentioned in paragraphs 0105 to 0131 of US2003/0157170.

The lipophilic component preferably comprises a pharmaceutically acceptable auxiliary. Of pharmaceutical acceptability are the auxiliaries that are known for use in the field of pharmacy, food technology and related fields, in particular the auxiliaries listed in relevant pharmacopoeia (e.g. DAB, Ph. Eur., BP, NF), as well as other auxiliaries whose properties do not preclude a physiological use.

Suitable cosmetically and pharmaceutically acceptable auxiliaries are also described in in Fiedler, H. P. Lexikon der Hilfsstoffe für Pharmazie, Kosmetik and angrenzende Gebiete [Lexicon of the auxiliaries for pharmacy, cosmetics and related fields], 4th edition, Aulendorf: ECV-Editio-Kantor-Verlag, 1996.

A further class of lipophilic components that can be encapsulated are compositions used for industrial or institutional or hospital applications.

Preferably, the lipophilic components comprise at least one composition used for industrial or institutional or hospital applications capable to dissolve the polyisocyanates employed in step b). More preferably, these are compositions used for industrial or institutional or hospital applications are capable to dissolve the polyisocyanates without extraneous solvents and/or auxiliaries. Should a composition used for industrial or institutional or hospital applications not ensure adequate solubility of the polyisocyanates, there is the option of overcoming this disadvantage by using suitable solubility promoters.

Suitable compositions used for industrial or institutional or hospital applications are, for example, chelants of heavy metal and hardness ions (builders), scale inhibiting agents, corrosion inhibiting agents, deflocculating/dispensing agents, stain removal agents, bleach stabilizing agents, protecting agents of peroxygen labile ingredients, photobleaching enhancing agents, thickener/viscosity modifying agents, crystal growth modification agents, sludge modification agents, surface modification agents, processing aids, electrolyte, hydrolytic stability agents, alkalinity agents and the like. The lipophilic components are compounds which are also useful for certain industrial applications, such as acid cleaners, aluminum etching, boiler cleaning, water treatment, bottle washing, cement modification, dairy cleaners, desalination, electrochemical machining, electroplating, metal finishing, paper mill evaporations, oil field water treatment, paper pulp bleaching, pigment dispersion, trace metal carrier for fertilizers, irrigation, circuit cleaning and the like.

A further class of lipophilic components that can be encapsulated are textile treatment compositions.

Preferably, the lipophilic components comprise at least one textile treatment composition capable to dissolve the polyisocyanates employed in step b). More preferably, these textile treatment compositions are capable to dissolve the polyisocyanates without extraneous solvents and/or auxiliaries. Should a textile treatment composition not ensure adequate solubility of the polyisocyanates, there is the option of overcoming this disadvantage by using suitable solubility promoters.

Suitable textile treatment compositions are softening compositions, such as liquid fabric softeners, fabric softening rinses, fabric softening sheets, tissue papers, paper towels, facial tissues, sanitary tissues, toilet paper and the like.

A further class of lipophilic components that can be encapsulated are vitamins. Suitable water-insoluble vitamins and provitamins are e.g. vitamin A, vitamin A acetate, vitamin D, vitamin E, tocopherol derivatives, such as tocopherol acetate and vitamin K.

Further, premix (II) comprises at least one polyisocyanate.

Isocyanates are N-substituted organic derivatives (R—N=C=O) of isocyanic acid (HNCO) tautomeric in the free state with cyanic acid. Organic isocyanates are compounds in which the isocyanate group (—N=C=O) is bonded to an organic radical. Polyfunctional isocyanates are compounds with two or more (e.g. 3, 4, 5, etc.) isocyanate groups in the molecule.

Preferably, the polyisocyanate employed in step b) comprises at least one difunctional isocyanate. In a special embodiment, the polyisocyanate employed in step b) is exclusively selected from difunctional isocyanates, the allophanates, isocyanurates, uretdiones or carbodiimides of difunctional isocyanates and mixtures thereof.

In general, suitable polyisocyanates are all aromatic, alicyclic and aliphatic isocyanates, provided they have at least two reactive isocyanate groups.

Preferably, the polyisocyanate component has an avarage content of 2 to 4 NCO groups. Preference is given to using diisocyanates, i.e. esters of isocyanic acid with the general structure O=C=N—R'—N=C=O, where R' is an aliphatic, alicyclic or aromatic radical.

Suitable polyisocyanates are chosen from compounds with 2 to 5 isocyanate groups, isocyanate prepolymers with an average number of from 2 to 5 isocyanate groups and mixtures thereof. These include, for example, aliphatic, cycloaliphatic and aromatic di-, tri- and higher polyisocyanates.

Preferably, the polyisocyanate is selected from hexamethylene diisocyanate (HDI), tetra-methylene diisocyanate, ethylene diisocyanate, 1,2-diisocyanatododecane, 4-isocyanatomethyl-1,8-octamethylene diisocyanate, triphenylmethane-4,4',4''-triisocyanate, 1,6-diisocyanato-2,2,4-trimethylhexane, 1,6-diisocyanato-2,4,4-trimethylhexane, isophorone diisocyanate (=3-Isocyanatmethyl-3,5,5-trimethylcyclohexylisocyanat, 1-Isocyanato-3-isocyanatomethyl-3,5,5-trimethyl-cyclohexan, IPDI), 2,3,3-trimethylhexamethylene diisocyanate, 1,4-cyclohexylene diisocyanate, 1-methyl-2,4-diisocyanatocyclohexane, dicyclohexylmethane-4,4'-diisocyanate (=methylene-bis(4-cyclohexylisocyanate)), 1,3-phenylene diisocyanate, 1,4-phenylene diisocyanate, 2,4- and 2,6-toluylene diisocyanate and isomer mixtures thereof, 1,5-naphthylene diisocyanate, 2,4'- and 4,4'-diphenylmethane diisocyanate (MOi), mixtures of diphenylmethane diisocyanates and more highly polycyclic homologs of diphenylmethane diisocyanate (polymeric MDI), hydrogenated 4,4'-diphenylmethane diisocyanate (H12MD1), xylylene diisocyanate (XDI), tetramethylxylol diisocyanate (TMXDI), 4,4'-dibenzyl diisocyanate, 4,4'-diphenyldimethylmethane diisocyanate, di- and tetraalkyldiphenylmethandiisocyanates, dimer fatty acid diisocyanates, chlorinated and brominated diisocyanates, 4,4'-diisocyanatophenylperfluoroethane, tetramethoxybutane-1,4-diisocyanate, phosphorus-containing diisocyanates, sulfur-containing diisocyanares, anionically modified polyisocyanates, polyethylene oxide-containing isocyanate, oligomers of the aforementioned polyisocyanates that contain urethane, allophanate, isocyanurate, uretdione, carbodiimide or biuret groups, and mixtures thereof.

Suitable chlorinated and brominated polyisocyanates comprise polyisocyanates with reactive halogen atoms. Preferably, the chlorinated and brominated polyisocyanate is selected from 1-chloromethylphenyl 2,4-diisocyanate, 1-bromomethylphenyl 2,6-diisocyanate, 3,3-bischloromethyl ether 4,4'-d iphenyldiisocyanate.

Suitable sulfur-containing polyisocyanates are obtained, for example, by reacting 2 mol of hexamethylene diisocyanate with 1 mol of thiodiglycol or dihydroxydihexyl sulfide.

Preferably, the anionically modified polyisocyanates contain at least two isocyanate groups and at least one anionic or aniogenic group in the molecule. Suitable anionic or aniogenic groups are carboxylic acid groups, sulfonic acid groups, phosphonic acids groups and the salts thereof. Preferably, the anionically modified polyisocyanates contain one or more than one sulfonic acid group or a salt thereof in the molecule. Suitable salts are e.g. sodium, potassium and ammonium salts. Ammonium salts are especially preferred. Preferred bases to neutralize the anionic groups are selected from, for example, ammonia, NaOH, KOH, $C_1$-$C_6$-alkylamines, preferably n-propylamine and n-butylamine, dialkylamines, preferably diethylpropylamine and dipropylmethylamine, trialkylamines, preferably triethylamine and triisopropylamine, $C_1$-$C_6$-alkyl-diethanolamines, preferably methyl- or ethyldiethanolamine and di-$C_1$-$C_6$-alkyl-ethanolamines.

Preferred anionically modified polyisocyanates are obtained by reaction of polyisocyanates with 2-(cyclohexylamino)-ethanesulfonic acid and/or 3-(cyclohexylamino)-propanesulfonic acid.

More preferred anionically modified polyisocyanates are obtained by reaction of polyisocyanates with 2-(cyclohexylamino)-ethanesulfonic acid and/or 3-(cyclohexylamino)-propanesulfonic acid, wherein the polyisocyanate is delected from hexamethylene diisocyanate, tetramethylene diisocyanate, isophorone diisocyanate, dicyclohexylmethane-4,4'-diisocyanate, 2,4- and 2,6-toluylene diisocyanate and isomer mixtures, diphenylmethane diisocyanates, biurets, allophanates and/or isocyanurates of the afore-mentioned polyisocyanates.

Suitable anionically modified polyisocyanates are described in US 2004/0034162 which is incorporated herein by reference.

Preferred anionically modified polyisocyanates have
an average isocyanate functionality of at least 1.8,
a content of isocyanate groups (calculated as NCO; molecular weight=42) of 4.0 to 26.0 wt. %,
a content of sulfonate groups (calculated as 503; molecular weight=80) of 0.1 to 7.7 wt. % and
optionally a content of ethylene oxide units bonded within polyether chains (calculated as $C_2H_2O$; molecular weight=44) of 0 to 19.5 wt. %, wherein the polyether chains contain a statistical average of 5 to 55 ethylene oxide units.

Preferred anionically modified polyisocyanates are selected from anionically modified hexamethylene diisocyanate, anionically modified hexamethylene diisocyanate, anionically modified isocyanurates of hexamethylene diisocyanate and mixtures thereof.

Preferred commercially available anionically modified polyisocyanates are modified isocyanurates of hexamethylene diisocyanate sold by Bayer AG under the trademark Bayhydur, e.g. Bayhydur XP. It has the following formula:

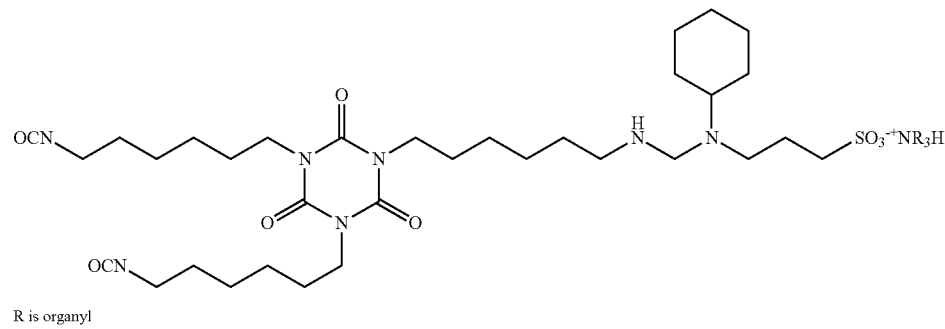

R is organyl

Suitable polyethylene oxide-containing polyisocyanates have at least two isocyanate groups and at least one polyethylene group. Polyethylene oxide-containing isocyanates are described, e.g. in U.S. Pat. No. 5,342,556. These isocyanates are self-emulsifying in water which may be advantageous within the context of the present process since it may be possible to dispense with a separate emulsifying step.

The polyisocyanate preferably comprises at least one polyisocyanate, selected from hexamethylene diisocyanate, tetramethylene diisocyanate, isophorone diisocyanate, dicyclo-hexylmethane-4,4'-diisocyanate, 2,4- and 2,6-toluylene diisocyanate and isomer mixtures thereof, 2,4'- and 4,4'-diphenylmethane diisocyanate, the biurets, allophanates and/or isocyanurates of the afore-mentioned polyisocyanates, anionically modified polyisocyanates, and mixtures thereof.

In a special embodiment, the polyisocyanate employed in step b) comprises two structurally different polyisocyanates (A) and (B).

Suitable polyisocyanates of type (A) are nonionic polyisocyanates bearing at least two NCO groups.

Preferably, polyisocyanates of type (A) are selected from hexamethylene diisocyanate, tetramethylene diisocyanate, dicyclohexylmethane-4,4'-diisocyanate, 2,4- and 2,6-toluylene diisocyanate and isomer mixtures thereof, 2,4'- and 4,4'-diphenylmethane diisocyanate and isomer mixtures thereof, the biurets, allophanates and/or isocyanurates of the afore-mentioned polyisocyanates or mixtures thereof.

In particular, isocyanates of type (A) are selected from hexamethylene diisocyanate, isophorone diisocyanate, dicyclohexylmethane-4,4'-diisocyanate, the isocyanurate of hexamethylene diisocyanate or mixtures thereof.

Preferred commercially available isocyanates of type (A) are hexamethylene diisocyanate sold by Bayer AG under the trademark Desmodur N3200™.

Also preferred commercially available isocyanates of type (A) are isophorone diisocyanate sold by Bayer AG under the trademark Desmodur N3300™.

The second polyisocyanate of type (B) is structurally different from the isocyanate of type (A). Preferably, the polyisocyanate of type (B) bears at least two NCO groups and at least one functional group, selected from anionic/anionogenic groups, polyethylene groups and combinations thereof.

Preferably, however, only anionically modified isocyanates are used as component (B) in the present process.

Preferably, the polyisocyanate (B) is selected from in each case anionically modified hexamethylene diisocyanate, tetramethylene diisocyanate, dicyclohexylmethane-4,4'-diisocyanate, 2,4- and 2,6-toluylene diisocyanate and isomer mixtures thereof, 2,4'- and 4,4'-diphenylmethane diisocyanate and isomer mixtures thereof, the biurets, allophanates and/or isocyanurates of the afore-mentioned polyisocyanates or mixtures thereof.

In particular, isocyanates of type (B) are selected from in each case anionically modified hexamethylene diisocyanate, isophorone diisocyanate, dicyclohexylmethane-4,4'-diisocyanate, the isocyanurate of hexamethylene diisocyanate or mixtures thereof.

In a prefered embodiment, the isocyanates of type (A) are selected from hexamethylene diisocyanate, isophorone diisocyanate, dicyclohexylmethane-4,4'-diisocyanate, the isocyanurate of hexamethylene diisocyanate or mixtures thereof and the isocyanates of type (B) are selected from anionically modified hexamethylene diisocyanate, anionically modified isophorone diisocyanate, anionically modified dicyclohexylmethane-4,4'-diisocyanate, the anionically modified isocyanurate of hexamethylene diisocyanate or mixtures thereof.

In a further preferred embodiment, the premix (II) comprises at least one nonionic polyisocyanate (A) and at least one anionically modified isocyanate (B), wherein the anionically modified diisocyanates (B) preferably contain at least one sulfonic acid group in the molecule.

In particular, the polyisocyanate of type (A) is hexamethylene diisocyanate, dicyclohexylmethane-4,4'-diisocyanate or a mixture thereof and the polyisocyanate of type (B) is anionically modified hexamethylene diisocyanate, anionically modified isocyanurate of hexamethylene diisocyanate, anionically modified dicyclohexylmethane-4,4'-diisocyanate or mixtures thereof.

The weight ratio of the polyisocyanates (A) and (B) is preferably in the range from 10:1 to 1:10, more preferably in the range from 5:1 to 1:5 and in particular in the range from 3:1 to 1:1.

It is also possible to use mixtures of different isocyanates of types (A) and (B). Besides the isocyanates (A) and (B), further isocyanates can also additionally be used in the process according to the invention.

In a further preferred embodiment of the present invention, the lipophilic component is used as the solvent for premix (II). Preferably, premix (II) contains no extraneous solvents apart from the lipophilic component.

Step c)

In step c) the premix (I) and premix (II) are mixed until an emulsion (III) is formed. In order to form an emulsion (III) in the present process, the premix (I) and premix (II) are emulsified e.g. by introducing energy into the mixture through stirring using a suitable stirrer until the mixture emulsifies.

A preferred embodiment is a process, wherein
a target range for the volume average diameter of the droplets of the hydrophobic (discontinuous phase) of the resulting emulsion (III) is predefined,
the actual volume average diameter of the droplets of the hydrophobic phase in the mixture of premix (I) and premix (II) is determined,
the speed of the stirrer and/or the time of stirring of the mixture are adjusted until the target value volume average diameter of the droplets of the hydrophobic phase of the resulting emulsion (III) is reached in order to obtain the predefined target volume average diameter of the droplets of the hydrophobic phase.

It has been found favourable if the mixture of premix (I) and premix (II) in step c) is stirred with a speed of the stirrer of 200 rpm to 1200 rpm, preferably 400 to 800 rpm. Those values are especially favorable if MIG stirrer is used.

It has been found favourable if the mixture of premix (I) and premix (II) is stirred vigorously in streaming conditions with Reynolds numbers above $10^3$ for a time period of only a several seconds up to a several minutes. The mixture in step c) is stirred for 1 to 120 minutes, preferably 2 minutes to 60 minutes, especially 5 to 20 minutes.

Suitable devices for controlling the volume average diameter of the droplets of discontinuous phase of the resulting emulsion are known to those skilled in the art. Such devises are based, for example, on light scattering measurements. Suitable light scattering measurements are known to those skilled in the art and are commercially available from, for example, Malvern Instruments, e.g. Malvern autosizer.

The rate of stirring of the mixture of premix (I) and premix (II) in step c) is adjusted to influence the size of droplets of hydrophobic phase in the aqueous phase. After a period of vigorous stirring, an emulsion is obtained, in which the premix (II) is dispersed as tiny droplets in the aqueous solution of premix (I). The droplets of the discontinuous phase of the emulsion has a volume average diameter of 15 to 88 μm.

The mixture of premix (I) and premix (II) is stirred vigorously. Preferred stirrer are MIG stirrer, propellers stirrer, paraviscs stirrer, INTERMIG stirrer and isojet stirrer.

The pH is preferably adjusted using aqueous bases, preference being given to using sodium hydroxide solution (e.g. 5% strength by weight). Preferably the pH of emulsion (III) is adjusted from 3 to 12, in particular between 4 to 10, and more particular in the range from 5 to 10.

In a preferred embodiment, premix (II) comprises a polyisocyanate (A) which is mixed with premix (I) until an emulsion is formed. Another polyisocyanate (B) is added to the obtained emulsion (III). In another preferred embodiment, the polyisocyanate (A) and polyisocyanare (B) are both contained in the premix (I). Preferably, first the isocyanate (A) is contained in the premix (II), and an emulsion with premix (I) is formed and the second the isocyanate (B) is added to the emulsion (III).

Step d)

The aqueous solution (IV) comprises at least one polyfunctional amine. Suitable amines are mentioned below. In a preferred embodiment, the aqueous solution comprises a bifunctional amine, preferably comprises or consists of at least one polyethyleneimine.

The emulsion (III) is stirred vigorously for a time period of only a few seconds up to several minutes. The aqueous solution (IV) is then be added to the emulsion (III) provided in step c).

In the sense of the invention, the term polyfunctional amine denotes amines that comprise at least two groups capable of reacting with NCO groups, wherein at least one of the groups capable of reacting with NCO groups is a primary or secondary amino group. When the polyfunctional amine contains only one primary or secondary amino group, it will contain one or more additional functional groups that are capable of reacting with NCO groups in a polymerisation reaction. Suitable are in principle active hydrogen atom containing groups. The groups of the polyfunctional amines that are reactive toward NCO groups are preferably chosen from hydroxyl groups and primary and secondary amino groups.

The polyfunctional amine is preferably selected from diamines, aminoalcohols, polymeric polyamines, guanidines, melamines, urea, hydrazines and mixtures thereof.

Suitable diamines are, for example, 1,2-ethylenediamine, 1,3-propylenediamine, 1,4-diamino-butane, 1,5-diaminopentane, 1,6-diaminohexane, 1,3-diamino-1-methylpropane, 1,4-diamino-cyclohexane, piperazin and mixtures thereof.

Suitable amino alcohols are, for example, 2-aminoethanol, 2-(N-methylamino)ethanol, 3-amino-propanol, 4-aminobutanol, 1-ethylaminobutan-2-ol, 2-amino-2-methyl-1-propanol, 4-methyl-4-aminopentan-2-ol, etc.

Suitable polymeric polyamines are in principle linear or branched polymers that have at least two primary or secondary amino groups. Additionally, these polymers can have tertiary amino groups in the polymer chain.

In the processes according to the invention, polyethyleneimines with a molecular weight of at least 500 g/mol, preferably from 600 to 30 000 or 650 to 25 000 g/mol and in particular from 700 to 10000 g/mol or 850 to 5000 g/mol, are preferably used.

Preference is given to polymeric polyamines having a weight-average molecular weight of at least 500 g/mol. More preferred are polymeric polyamines having a weight-average molecular weight of from 500 to 1000000, in particular from 650 to 2000000, especially from 700 to 100000, more especially from 800 to 50000.

The polymeric polyamine is preferably selected from polyalkyleneimines, polyvinylamines, polyetheramines, etc. More preferably, the polymeric polyamine is selected from poly-alkyleneimines, in particular polyethyleneimines.

Preferred polyethyleneimines are diethylenetriamine, triethylenetetramine, tetraethylene-pentamine, ethylenepropylenetriamine, trisaminopropylamine and higher polyethyleneimines.

In a preferred embodiment, the polymeric polyamine is selected from polyethyleneimines having a weight average molecular weight of at least 300 g/mol. Suitable polyethyleneimines contain the following repeat units

wherein
x is from 8 to 1500, preferably from 10 to 1000;
y is from 0 to 10, preferably from 0 to 5, especially 0;
z is 2+y.

Preferred polyethyleneimines are linear polyethyleneimines, wherein x is from 8 to 1500, y is 0 and z is 2.

Preferred commercially available polyethylenimines are sold by BASF SE under the trademark Lupasol™ and the Jeffamine trademarks from Huntsman, particularly Lupasol™ PR8515.

In the processes according to the invention, polyethyleneimines with a molecular weight of at least 500 g/mol, preferably from 600 to 30 000 or 650 to 25 000 g/mol and in particular from 700 to 5000 g/mol or 850 to 2500 g/mol, are preferably used.

It is preferred to use the ratio of amine molar equivalents (both primary and secondary) in the polyethyleneimine to Isocanate molar equivalents contained in the isocyanate compound (A) or (A) and (B) from 1.0:1.0 to 1.0:1.5, especialy from 1.0:1.05 to 1.0:1.2.

Step e)

The polyaddition reaction in step e) is generally performed at a temperature of at least 50° C., preferably 60° C., more preferably in a range of from 75° C. to 90° C. and in particular 85° C. to 90° C., in order to ensure sufficiently rapid reaction progress.

Here, it may be preferred to increase the temperature in stages (e.g. in each case by 10° C.) until the completion of the reaction.

The reaction time typically depends on the reaction amount and temperature used. The period of time for the polyaddition reaction is ranging from a few minutes to several hours. Usually, microcapsule formation is established between ca. 60 minutes to 6 h or up to 8 h at the temperatures defined above.

Step f)

According to the invention in step f) the addition of hydroxyalkylcellulose to the dispersion obtained in step e) is required.

In addition to hydroxyalkylcelluloses, the microcapsule dispersion of the invention may comprise at least one stabilizing agent which is different from hydroxyalkylcelluloses. Suitable further stabilizing agents different from hydroxyalkylcelluloses are described in the following.

The relation to hydroxyalkylcellulose the term "alkyl" is preferably defined as linear or branched $C_1$-$C_6$ alkyl. Examples of $C_1$-$C_6$-alkyl are $CH_3$, $C_2H_5$, n-propyl, $CH(CH_3)_2$, n-butyl, $CH(CH_3)$—$C_2H_5$, $CH_2$—$CH(CH_3)_2$, $C(CH_3)_3$, n-pentyl, 1-methylbutyl, 2-methylbutyl, 3-methylbutyl, 2,2-dimethyl-propyl, 1-ethylpropyl, n-hexyl, 1,1-dimethylpropyl, 1,2-dimethylpropyl, 1-methylpentyl, 2-methyl-pentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethyl-propyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl.

Examples of $C_2$-$C_6$-hydroxyalkyl groups are 2-hydroxyethyl, 2- and 3-hydroxypropyl, 1-hydroxy-prop-2-yl, 3- and 4-hydroxybutyl, 1-hydroxybut-2-yl, 5-hydroxypentyl, 6-hydroxyhexyl. Preferred is 2-hydroxyethyl.

Preferred is hydroxyalkylcellulose, wherein alkyl is a $C_1$-$C_4$-alkyl, particularly hydroxyethyl-cellulose. Suitable hydroxyalkylcelluloses can be prepared by alkoxylation of a cellulose material by known methods. Thus, a cellulose can be reacted with ethylene oxide and/propylene oxide. The amount of alkylene oxide is preferably about 0.01 to 5 moles, more preferably about 0.02 to 3.5 moles, especially 0.05 to 2.5 per mole of glucose repeat units in the employed cellulose.

Preferably, the hydroxyalkylcellulose has a degree of polymerization (DP) of 10 to 5000, preferably 20 to 3000, in particular 30 to 1000.

Preferably, the hydroxyalkylcellulose has a degree of substitution with respect to hydroxyalkyl groups (DS) of from 0.01 to 3, more preferably 0.02 to 2, especially 0.02 to 1.5.

Preferred commercially available hydroxyalkylcelluloses are the Natrosol™ trademarks and especially preferred Natrosol™ 250 (CAS-Nr. 9004-62-0) of Herkules Incorporated.

In a particular embodiment of the invention, the amount of hydroxyalkylcellulose employed in the dispersion is in the range from 0.01% by weight to 1.2% by weight, more particularly in the range from 0.01% by weight to 0.6% by weight, based on the total weight of the dispersion.

Provided hydroxyalkylcellulose is employed as a stabilizing agent, additional stabilizing agents may also be employed. Examples of suitable additional stabilisation agents are starches, acrylate homopolymers or acrylate copolymers.

Preferred commercially available starches are sold by National starch, under the trademark National 465, Purity W or starch B990.

Preferred commercially available acrylate polymers or copolymers are sold by BASF SE under the trademark Tinovis CD, Ultragel 300 and Rheocare TTA.

When additional stabilizing agents are employed, they may be used in an amount of about 0.1% by weight to about 5.0% by weight, particularly 0.5% by weight to 4% by weight and more particularly 1% to 3% by weight, based on the total weight of the dispersion.

The stabilizing agent, in particular hydroxyalkylcellulose, is preferably added to the dispersion once the microcapsules are formed. It is not preferred to add the stabilizing agent, in particular hydroxyalkylcellulose, during the formation of the microcapsules.

In a special embodiment, the hydroxyalkylcellulose is added to the microcapsule dispersion in combination with at least one dispersion aid. Examples of suitable dispersion aids are alcohols, polyols, mono- and dialkyether of polyols, oils and mixtures thereof.

Suitable dispersion aids are alkylenglycoles, alkylengly-colmono($C_1$-$C_4$-alkyl)ethers, alkylen-glycoldi($C_1$-$C_4$-alkyl) ethers, polyalkylenglycoles, polyalkylenglycolemono($C_1$-$C_4$-alkyl)ethers, polyalkylenglycoledi($C_1$-$C_4$-alkyl)ethers and mixtures thereof.

The dispersion aid is preferably selected from methanol, ethanol, n-propanol, isopropanol, n-butanol, ethylenglycol, ethylenglycolmono($C_1$-$C_4$-alkyl)ethers, ethylenglycoldi($C_1$-$C_4$-alkyl)ethers, 1,2-propylenglycol, 1,2-propylenglycolmono($C_1$-$C_4$-alkyl)ethers, 1,2-propylenglycoldi($C_1$-$C_4$-alkyl) ethers, glycerin, polyglycerines and mixtures thereof.

Preferred dispersion aids are glycerine or propandiol.

A further aspect of the invention relates to the process according to the invention, wherein the the obtained microcapsules, as described above, may be dryed to provide microcapsules in solid form, preferably in form of a powder.

Step g)

According to one embodiment of the invention the microcapsules obtained in step f) can be dried. So, the process according to the invention comprising in addition g) subjecting the microcapsules obtained in step f) to a drying.

The microcapsules obtained in step f) may be dried using techniques known in the art. For example, the solid capsules can be isolated by filtration and dryed. Drying of the isolated capsules may be performed by heating, e.g. in an oven or by contact with a heated gas stream.

Preferably, drying of the dispersion is carried out by spray drying or fluid-bed drying.

Spray drying techniques and apparatus are well known in the art. A spray-drying process pushes suspended capsules through a nozzle and into a drying chamber. The capsules may be entrained in a fluid (such as air) that moves inside of a drying chamber. The fluid (which may be heated, for example at a temperature of 150 and 120° C., more preferably between 170° C. and 200° C., and still more preferably between 175° C. and 185° C.) causes the liquid to evaporate, leaving behind the dried capsules which can then be collected from the process equipment and further processed.

It is conventional to mix spray dried capsules with flow aids to produce a flowable powder that are not susceptible to caking. Flow aids include silicas or silicates, such as precipitated, fumed or colloidal silicas; starches; calcium carbonate; sodium sulphate; modified cellulose; zeolites; or other inorganic particulates known in the art.

It is quite common, given the high temperatures and impaction forces encountered during a spray drying procedure, for core shell capsules to lose some of their core material.

Furthermore, it may not be possible to work at sufficiently high temperatures for a sufficiently long period of time to drive off all moisture from the dispersion, without compromising the thermal stability of the capsules. Accordingly, the polyurea capsules emerging from a spray-drying process, as herein described, may contain small amounts of surface oil as well as residual moisture.

A further embodiment of the invention relates to microcapsules obtained by the process defined above from step a) to step f) in form of an aqueous dispersion.

One important parameter of the dispersion of microcapsules of the invention is the shell weight of the capsules in relation to the total weight of the capsules. It is expressed as percentage of the shell weight with reference to the total weight of the capsules (=encapsulated lipophilic component+shell material).

The percentage of the shell weight with reference to the total weight of the capsules is of 3% to 40%, particularly 5% to 25%, and more particularly 10% to 20%.

The shell weight is an important parameter in determining both the stability of the microcapsules and the performance characteristics of the dispersion of microcapsules of the present invention. In particular, the shell weight in relation to the volume average diameter of the capsules determines the release characteristics of the encapsulated lipophilic components. Especially, the stability and performance of the capsules is in an advantageous range if the ratio of the shell weight which is expressed as percentage of the shell weight with reference to the total weight of the capsules, to the capsule volume average diameter is $\leq 0.7$ $\mu m^{-1}$, preferably $\leq 0.6$ $\mu m^{-1}$, more preferably $\leq 0.5$ $\mu m^{-1}$, and in particular $\leq 0.2$ $\mu m^{1}$.

It has been found that shell weight to capsule volume ratio is a more reliable parameter than shell thickness for in-process control. By manipulating shell weight to capsule volume ratio which means simply by controlling the amount of shell-forming monomers added during the encapsulation process, and the capsule diameter within the parameters described above, it is possible to produce microcapsules with at least one encapsulated lipophilic component having the required release profile for all purposes of the invention. More particularly, microcapsules which are sufficiently mechanically robust when they are subjected to compression or shear force that does not exceed a critical value can be obtained. This enables the encapsulated liophilic components to be incorporated effectively in leave-on products, such as deodorant sticks, hair conditioners, skin care products including creams, lotions and shaving products, whilst retaining the capability of being sheared by frictional contact between material and material, when in use.

The microcapsules obtained by the process according to the invention, typically have core/shell ratios (w/w) from 20:1 to 1:1, preferably from 5:1 to 2:1 and in particular from 4:1 to 3:1.

Further, the present invention relates to a microcapsule dispersion, wherein the viscosity of the dispersion is preferably $\leq 4$ Pa s, more preferably in the range from 0.15 to 3 Pa s, when measured on a rheometer, for example a RheoStress™ 1 instrument (ThermoScientific), using rotating disks at a shear rate of 21 $s^{-1}$ at a temperature of 25° C.

Preferably, the nominal rupture stress of the microcapsules, expressed as MPa, is in the range of 0.1 to 2 MPa, particularly 0.2 to 1.5 MPa and more particularly 0.4 to 1 MPa.

If the microcapsules of the present invention are intended to be stored in the form of a dispersion, the pH of the dispersion is adjusted to a level of about 5 to 10. This may be achieved with the addition to an alkaline dispersion of a suitable acid, such as citric acid or formic acid.

The microcapsule composition can be prepared continuously or batchwise, preferably batchwise.

In a further embodiment, the dispersion of the microcapsules may contain non-encapsulated, i.e. free lipophilc components, external of the capsules in the aqueous dispersion.

It is likewise possible for the ingredients of the core to migrate from the core of the microcapsules (i.e. the lipophilic component and/or further materials present in the core) into the shell.

In a further embodiement of the invention, the dispersion of the microcapsules comprises at least one preservative in order to prevent microbial contamination of the microcapsules. The preservative may be encapsulated and/or it may be contained in the aqueous suspending medium of the dispersion.

Suitable preservatives include quaternary compounds, biguanide compounds, ethylhexylglycerin, caprylyl glycol, phenezhyl alcohol, propandiol, undecyl alcohol, tocopherol and mixtures thereof.

Non-limiting examples of quaternary compounds include benzalkonium chlorides and/or substituted benzalkonium chlorides, di($C_6$-$C_{14}$)alkyl di short chain ($C_{1-4}$ alkyl and/or hydroxyalkl) quaternary, N-(3-chloroallyl) hexaminium chlorides, benzethonium chloride, methylbenzethonium chloride, cetylpyridinium chloride, diester quaternary ammonium compounds and mixtures thereof.

Preferred commercially available benzalkonium chlorides are sold by Lonza under the trademark Barquat®, Maquat® trademarks from Mason, Variquat® trademarks from Witco/Sherex and Hyamine® trademarks from Lonza.

Preferred commercially available di($C_6$-$C_{14}$)alkyl di short chain ($C_{1-4}$ alkyl and/or hydroxyalkl) quaternary are sold by Lonza under the trademark Bardac®.

Preferred commercially available N-(3-chloroallyl) hexaminium chlorides are sold by Dow under the trademark Dowicide® and Dowicil®.

Preferred commercially available benzethonium chlorides are sold by Rohm & Haas under the trademark Hyamine®.

Preferred commercially available methylbenzethonium chlorides are sold by Rohm & Haas under the trademark Hyamine® 10*.

Preferred commercially available cetylpyridinium chlorides are sold by Merrell Labs under the trademark Cepacol chloride.

Examples of preferred dialkyl quaternary compounds are di($C_8$-$C_{12}$)dialkyl dimethyl ammonium chlorides.

Preferred commercially available dialkyl quaternary and dioctyldimethylammonium chlorides are sold by Lonza under the trademark Bardac® 22 and (Bardac® 2050).

The quaternary compounds useful as cationic preservatives and/or antimicrobial agents herein are preferably selected from the group consisting of dialkyldimethylammonium chlorides, alkyldimethylbenzylammonium chlorides, dialkylmethylbenzylammonium chlorides, and mixtures thereof. Other preferred cationic antimicrobial actives useful herein include diisobutylphenoxyethoxyethyl dimethylbenzylammonium chloride and (methyl)diisobutyl-phenoxyethoxyethyl dimethylbenzylammonium chloride (i.e. methylben-zethonium chloride).

Preferred commercially available quaternary compounds are sold by Rohm & Haas under the trademark Hyamine® 1622.

Preferred commercially available preservatives are sold by Schülke under the trademark Sensiva® PA20, Sensiva® PA40, Sensiva® SC10, Sensiva® SC50.

The microcapsules and dispersion of the microcapsules as defined above can be used in a large number of different applications, depending on the type of lipophilic components.

A preferred embodiment of the invention is the use of the microcapsules prepared by the process acoording to the invention for a personal care composition or a composition used for industrial or institutional or hospital disinfection or a material protection composition or a pharmaceutical composition or a plant protection composition, a home care product.

A preferred embodiment of the invention is the use of the microcapsules prepared by the process acoording to the invention for a cosmetic composition or a hygiene composition or a composition for industrial or institutional or hospital cleaning or disinfection or laundry detergents, fabric softeners, dishwashing liquids, household cleaners or industrial cleaners.

Preference is given to using the microcapsules for the finishing of all kind of nonwovens, like wipes (for example wet wipes or dry wipes for cosmetic or cleaning purposes), but also for finishing papers (including wallpapers, toilet paper or papers for books and newsletters), for finishing diapers or sanitary napkins and similar hygienic products or textiles, e.g. in order to finish the papers or textiles with a dye or an insecticide, or in cosmetic compositions, e.g. for producing sunscreen compositions which comprise the UV filter in the form of the microcapsules. Another use pertains to finishing diapers or sanitary napkins and similar hygienic products. Furthermore, the microcapsules may be used in massage oils or cremes or personal lubricants, and suppositories, e.g. to provide this products with antiinflammatory actives.

A preferred embodiment of the invention is the use of the microcapsules prepared by the process acoording to the invention in finishing of textiles, papers or nonwovens.

EXAMPLES

The following examples are intented to further illustrate the present invention without limiting its scope in any way.

Analytics

The volume average particle size is measured by light scattering measurements using a Malvern 2000S instrument and the Mie scattering theory, e.g. Mictrotrac nanotrac 250.

Young's modulus (E-Modulus) and Nominal rupture stress are described above. In Particular, in order to get quantitative mechanical information of the microcapsule surface the Peak-Force Quantitative Nano-Mechanics mode (PF-QNM) is used.

Ingredients polyvinylpyrrolidone having a K value of 90 (PVP Kolloidon 90 by BASF SE)

caprylic/capric triglyceride (Myritol® 318 by BasF SE)

dicyclohexylmethane diisocyanate (Desmodur® W)

anionic HDI oligomer (Bayhydur® XP 2547 by Bayer Material Science)

polyethyleneimine (Lupasol® PR8515 by BASF SE)

hydroxyethylcellulose (Natrosol® 250 by Herkules)

Preparation

Example 1. (With the Ratio of Capsule Shell to Capsule Diameter <0.7)

A premix(I) was prepared from 25 g of polyvinylpyrrolidon having a K value of 90 (PVP Kollidon 90) and 860 g of water and adjusted to a pH of 10.0 using aqueous sodium hydroxide solution (5% strength by weight). Premix II was prepared from 300 g of caprylic/capric triglyceride (Myritol® 318), 23.8 g of dicyclohexylmethane diisocyanate (Desmodur® W) and 6.6 g of anionic HDI oligomer (Bayhydur® XP 2547). These two premixes were combined and emulsified with the help of a Mig stirrer at room temperature and a speed of 800 rpm until the desired capsule size was achieved monitored with a Malvern Autosizer. The pH of the emulsion was then adjusted to 8.5 using aqueous sodium hydroxide solution (5% strength by weight). Then, at room temperature and with stirring at 800 rpm, a solution of 12 g of polyethyleneimine (Lupasol® PR8515) in 22.6 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. Finally, 5 g of hydroxyethylcellulose (Natrosol® 250) was added at once. The mixture was then cooled to room temperature, giving the desired microcapsule dispersion with the volume particle size distribution according to the following values: d 50=40 μm and d 90=78 μm.

$$\frac{\text{shell weight}}{\text{capsule diameter}} = 0.45$$

Young's modulus: ~100 MPa

Nominal rupture stress: 0.1-0.5 MPa

Example 2. (With the Ratio of Capsule Shell to Capsule Diameter<0.7)

A premix(I) was prepared from 25 g of polyvinylpyrrolidon having a K value of 90 (PVP Kollidon 90) and 870.4 g of water and adjusted to a pH of 10.0 using aqueous sodium hydroxide solution (5% strength by weight). Premix II was prepared from 300 g of caprylic/capric triglyceride (Myritol® 318), 19.9 g of dicyclohexylmethane diisocyanate (Desmodur® W) and 5.5 g of anionic HDI oligomer (Bayhydur® XP 2547). These two premixes were combined and emulsified with the help of a Mig stirrer at room temperature and a speed of 400 rpm until the desired capsule size was achieved. The pH of the emulsion was then adjusted to 8.5 using aqueous sodium hydroxide solution (5% strength by weight). Then, at room temperature and with stirring at 800 rpm, a solution of 10.2 g of polyethyleneimine (Lupasol® PR8515) in 19 g of water was added over the course of 1 minute. The reaction mixture was then subjected to the following temperature program: heating to 60° C. in 60 minutes, maintaining this temperature for 60 minutes, then 60 minutes at 70° C., 60 minutes at 80° C. and finally 60 minutes at 85° C. Finally, 5 g of hydroxyethylcellulose (Natrosol® 250) was added at once. The mixture was then cooled to room temperature, giving the desired microcapsule dispersion with the volume particle size distribution according to the following values: d 50=33 µm and d 90=56 µm.

$$\frac{\text{shell weight}}{\text{capsule diameter}} = 0.5$$

Young's modulus: ~30 MPa
Nominal rupture stress: <0.2

Examples 3 and 4 and Comparison Examples; Phase Separation

According to example 1 microcapsules were prepared, but with different stabilizing agents in step (f). As shown in table 1 the use of hydroxyethylcellulsose alone or in mixture with a second stabilizing agent give microcapsule dispersion with a better stability (lower phase separation after 2 weeks according to example 1, 3 and 4 in comparison to the examples without hyroxyethylcellulose).

| stabilizing agent in step (f) | amount tested [%] [1] | phase separation after 2 weeks at 50° C. [%] [2] |
|---|---|---|
| Rheocare XG | 3.0 | >20 |
| Rheocare TTA | 3.0 | >20 |
| Luvigel Fit | 3.0 | >20 |
| Tinovis ADE | 3.0 | >20 |
| Luvigel Star | 3.0 | >20 |
| Tinovis CD | 3.0 | >10 |
| Cosmedia Triple C | 3.0 | >20 |
| Cosmedia SP | 3.0 | >20 |
| Purity W | 3.0 | 10 |
| Starch B990 | 3.0 | 10 |
| National 465 | 3.0 | 10 |
| Natrasol 250 (Example 1) | 0.4 | >5 |
| Natrosol 250 with Cosmedia Triple C (Example 3) | 0.2:1.5 | >5 |
| Natrosol 250 with Purity W (Example 4) | 0.2:1.5 | >5 |

[1] Percentage by weight
[2] Stabilization was measured by naked eye assessment and was expressed as the ratio of the height of the water phase to the total height of the slurry Stabilizing agents in step (f)
Rheocare® XG Xanthan gum
Rheocare® TTA Acrylates Copolymer
Luvigel® Fit Acrylates/C10-C30 Alkyl Methacrylate Copolymer
Tinovis® ADE Sodium acrylates copolymer (and) hydrogenated polydecene (and) PPG-1 Trideceth-6
Luvigel® Star Polyurethane-39
Tinovis® CD Dimethylacrylamide/Ethyltrimonium chloride Methacrylate Copolymer (and) Propylene gylcol dicaprylate/dicaprate (and) PPG-1 Trideceth-6 (and) C10-C11 Isoparaffin
Cosmedia® Triple C Polyquaternium-37 (and) Dicaprylyl Carbonate (and) Lauryl Clucoside
Cosmedia® SP Sodium Polyacrylate
Purity® W modified starch
Starch® B990 modified starch
National® 465 modified starch
Natrosol® 250 hydroxyethyl cellulose by Herkules HR

The invention claimed is:

1. A process for preparing microcapsules, wherein the microcapsules have a volume average diameter d 50 of 15 to 90 µm and a percentage of the shell weight of 3 to 40%, with reference to the total weight of capsules, wherein a shell of the microcapsules comprises at least one polyurea and a core comprises at least one lipophilic component with the proviso that the core does not contain a fragrance, comprising the steps of:
   a) providing a premix (I) comprising at least one protective colloid different from a hydroxyalkylcellulose in an aqueous solution,
   b) providing a premix (II) comprising at least one polyisocyanate and at least one lipophilic component,
   c) mixing premix (I) and premix (II) until an emulsion (III) is formed,
   d) adding an aqueous solution (IV) containing at least one polyfunctional amine to the emulsion formed in step c),
   e) forming a dispersion of microcapsules by heating the mixture obtained in step d) to a temperature of at least 50° C. until microcapsules are formed, and
   f) adding the hydroxyalkylcellulose to the dispersion obtained in step e), wherein the amount of the hydroxyalkylcellulose is 0.01 to 1.2% by weight based on the total weight of the dispersion.

2. The process according to claim 1, wherein droplets of a discontinuous phase of the emulsion (III) has a volume average diameter d 50 of 15 to 88 µm.

3. The process according to claim 1, wherein the hydroxyalkylcellulose comprises at least one hydroxyethylcellulose.

4. The process according to claim 1, wherein the hydroxyalkylcellulose is added with an additional stabilizing agent.

5. The process according claim 1, comprising in addition
   g) subjecting the microcapsules obtained in step f) to a drying.

6. The process according to claim 1, wherein the premix (I) comprises a protective colloid selected from polyvinylpyrrolidones, polyvinyl alcohols, and mixtures thereof.

7. The process according to claim 1, wherein the protective colloid employed in step a) comprises at least one polyvinylpyrrolidone.

8. The process according to claim 1, wherein the lipophilic component is selected from active substances and additives for personal care compositions, home care compositions, compositions used for industrial or institutional or hospital applications, material protection compositions, pharmaceutical compositions, or plant protection compositions.

9. The process according to claim 1, wherein the lipophilic component is selected from the group consisting of oil bodies, UV-filters, organic compounds, biocides, dyes, emollients, vitamins, cosmetically active ingredients, pharmaceutically ingredient, cosmetically and pharmaceutically acceptable auxiliaries, detergents, or and mixtures thereof.

10. The process according to claim 9, wherein the premix (II) comprises at least one nonionic polyisocyanate (A) and at least one anionically modified isocyanate (B), wherein the anionically modified diisocyanate (B) contains at least one sulfonic acid group in the molecule.

11. The process according to claim 9, wherein the premix (II) comprises at least one polyisocyanate (A) selected from the group consisting of hexamethylene diisocyanate, tetramethylene diisocyanate, dicyclohexylmethane-4,4'-diisocyanate, 2,4- and 2,6-toluylene diisocyanate and isomer mixtures thereof, 2,4'- and 4,4'-diphenylmethane diisocyanate and isomer mixtures, biurets, allophanates, isocyanurates and mixtures thereof.

12. The process according to claim 9, wherein the premix (II) comprises at least one polyisocyanate (B) selected from the group consisting of anionically modified hexamethylene diisocyanate, anionically modified tetramethylene diisocyanate, anionically modified dicyclohexylmethane-4,4'-diisocyanate, anionically modified 2,4- and 2,6-toluylene diisocyanate and isomer mixtures thereof, anionically modified 2,4'- and 4,4'-diphenylmethane diisocyanate, the anionically modified biurets, anionically modified allophanates, isocyanurates, and mixtures thereof.

13. The process according to claim 12, wherein the weight ratio of isocyanates (A) and (B) is in the range from 10:1 to 1:10.

14. The process according to claim 9, wherein the polyfunctional amine is a bifunctional amine.

15. The process according to claim 9, wherein a core-shell ratio (w/w) of the microcapsules is 20:1 to 1:1.

16. A microcapsule dispersion comprising:
   a dispersion of microcapsules in an aqueous medium obtained by the process of claim 9, wherein a hydroxyalkylcellulose is present the dispersion in an amount from 0.01 to 1.2% by weight based on the total weight of the dispersion.

17. A composition selected from the group consisting of personal care composition, home care composition, antimicrobial disinfection composition, pharmaceutical composition, and plant protection composition, the composition comprising the microcapsule composition of claim 16.

18. A composition selected from the group consisting of cosmetic composition, hygiene composition, antimicrobial disinfection composition, a laundry detergent, fabric softener, dishwashing liquid, household cleaner, and industrial cleaner, the composition comprising the microcapsule composition of claim 16.

19. An article selected from textile, paper and nonwoven material, the article comprises the microcapsule composition of claim 16.

* * * * *